(12) United States Patent
Galiana et al.

(10) Patent No.: US 8,886,578 B2
(45) Date of Patent: Nov. 11, 2014

(54) METHOD AND SYSTEM FOR AUTOMATICALLY CLASSIFYING AND IDENTIFYING VESTIBULO-OCULAR RESPONSES

(75) Inventors: Henrietta Galiana, St Lambert (CA); Atiyeh Ghoreyshi, Brossard (CA)

(73) Assignee: The Royal Institution for the Advancement of Learning/McGill University, Montreal (CA)

( * ) Notice: Subject to any disclaimer, the term of this patent is extended or adjusted under 35 U.S.C. 154(b) by 306 days.

(21) Appl. No.: 13/347,743

(22) Filed: Jan. 11, 2012

(65) Prior Publication Data

US 2012/0179636 A1 Jul. 12, 2012

Related U.S. Application Data

(60) Provisional application No. 61/431,617, filed on Jan. 11, 2011.

(51) Int. Cl.
| | | |
|---|---|---|
| *G06F 15/18* | (2006.01) | |
| *A61B 5/00* | (2006.01) | |
| *A61B 5/11* | (2006.01) | |
| *A61B 3/113* | (2006.01) | |

(52) U.S. Cl.
CPC ............ *A61B 5/4863* (2013.01); *A61B 5/1114* (2013.01); *A61B 3/113* (2013.01); *A61B 5/7264* (2013.01)
USPC .......................................................... 706/14

(58) Field of Classification Search
None
See application file for complete search history.

(56) References Cited

U.S. PATENT DOCUMENTS 5,819,247 A * 10/1998 Freund et al. ................... 706/25

OTHER PUBLICATIONS

Vidal et al. "DynamicBoost: Boosting Time Series Generated by Dynamical Systems", ICCV, 2007, pp. 6.*
Barnes, G. R. "A procedure for the analysis of nystagmus and other eye movements." Naval Aerospace Medical Research Laboratory, Jun. 1981 (21 pages).
Behrens, F. and L. Weiss "An algorithm separating saccadic from nonsaccadic eye movements automatically by use of the acceleration signal." Vision research 32(5): 889-893 (1992).
Cohen, B., V. Henn, T. Raphan and D. Dennett "Velocity storage, nystagmus, and visual-vestibular interactions in humans." Ann N Y Acad Sci 374: 421-33. (1981).
Faucheux, S., B. Schwaller and A. Buizza "Automatic detection and removal of fast phases from nystagmographic recordings by optimal thresholding." Biomedical Signal Processing and Control 2(2): 144-150 (2007).

(Continued)

*Primary Examiner* — Li-Wu Chang
(74) *Attorney, Agent, or Firm* — The Law Office of Michael E. Kondoudis

(57) ABSTRACT

Stabilizing the visual system for any sighted mobile system increases immunity of the mobile system's gaze and reduces information processing task complexity. Two human reflexes are the optokinetic reflex and vestibulo-ocular reflex (VOR). The VOR stabilizes retinal images during head movement by producing eye movements in the opposite direction. Improved analysis of the VOR in humans would improve the diagnosis/treatment of patients, provide improvements in visual prosthesis performance for patients, and also vision systems performance for mobile robotic systems. However, an important issue for prior art mathematical analysis techniques is the requirement to classify the nystagmus segments before applying any analysis techniques, wherein this classification should be preferably performed non-subjectively. Accordingly the inventors overcome these limitations by performing classification, i.e. segmentation of the data record into multiple modes (including possible artifacts or outliers), and identification of mode dynamics concurrently and objectively in a manner suitable for multi-input systems.

12 Claims, 18 Drawing Sheets

(56) References Cited

OTHER PUBLICATIONS

Juhola, M., H. Aalto and T. Hirvonen "A signal analysis technique of vestibulo-ocular reflex stimulated with impulsive head movements." Ann Biomed Eng 34(7): 1213-25 (2006).

Galiana, H. L. "A nystagmus strategy to linearize the vestibulo-ocular reflex." IEEE Trans Biomed Eng 38(6): 532-43 (1991).

Ghoreyshi, A. and H. L. Galiana "A hybrid extended least squares method (HybELS) for vestibulo-ocular reflex identification" Engineering in Medicine and Biology Society, 2009. EMBC 2009. Annual International Conference of the IEEE (2009).

Ghoreyshi, A. and H. L. Galiana "GNL-HybELS: An algorithm to classify and identify VOR responses simultaneously" Engineering in Medicine and Biology Society, EMBS, Buenos Aires, (2010).

Ghoreyshi, A. and R. Vidal "Segmenting dynamic textures with ising descriptors, ARX models and level sets." Dynamical Vision 4358 (2007).127-141.

Kukreja, S. L., R. E. Kearney and H. L. Galiana "A least-squares parameter estimation algorithm for switched hammerstein systems with applications to the VOR." IEEE Trans Biomed Eng 52(3): 431-44 (2005).

Lu, L. and R. Vidal Combined central and subspace clustering for computer vision applications, ACM (2006).

Rey, C. G. and H. L. Galiana "Parametric classification of segments in ocular nystagmus." IEEE Trans Biomed Eng 38 (2): 142-8 (1991).

Rey, C. G. and H. L. Galiana "Transient analysis of vestibular nystagmus." Biol Cybern 69(5-6): 395-405 (1993).

Vidal, R., Y. Ma and S. Sastry "Generalized principal component analysis (GPCA)." IEEE Transactions on Pattern Analysis and Machine Intelligence 27(12): 1945-1959 (2005).

* cited by examiner

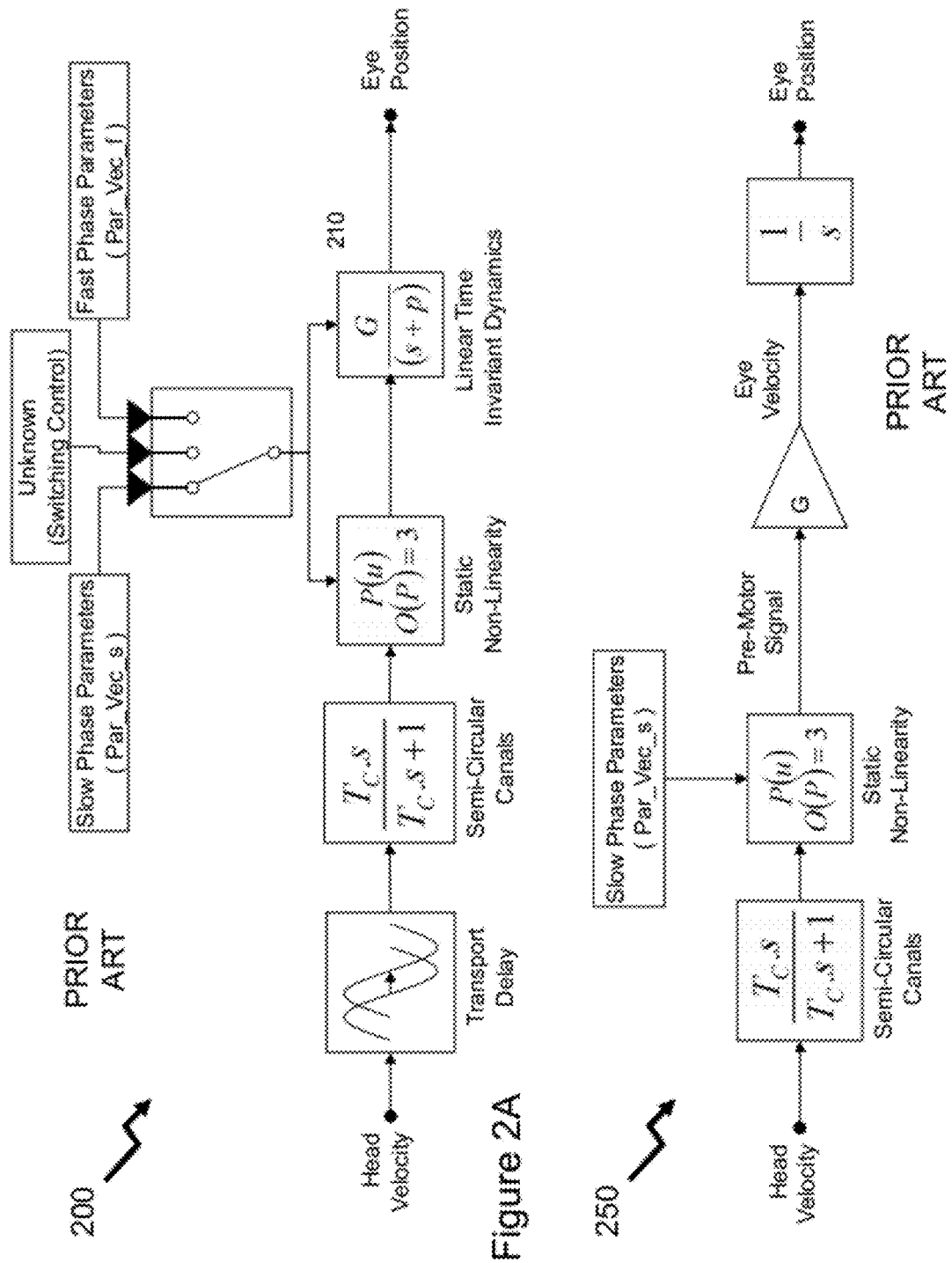

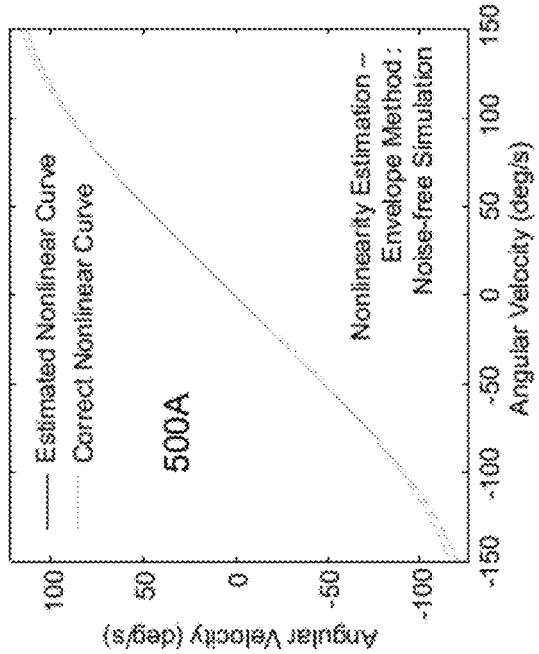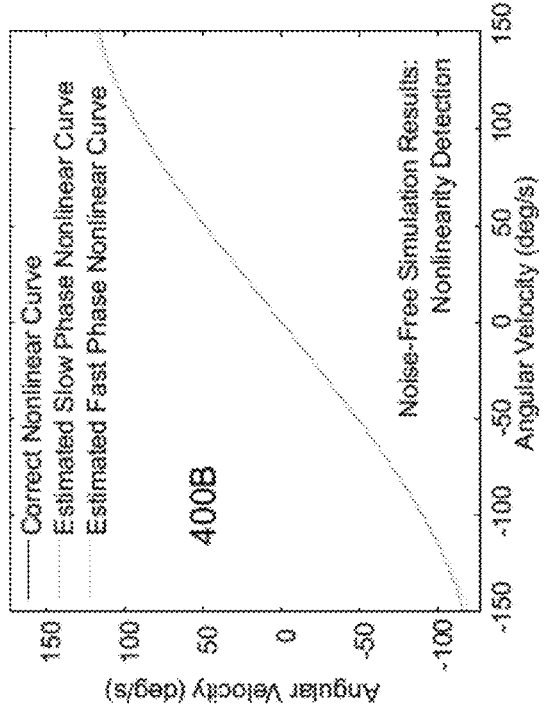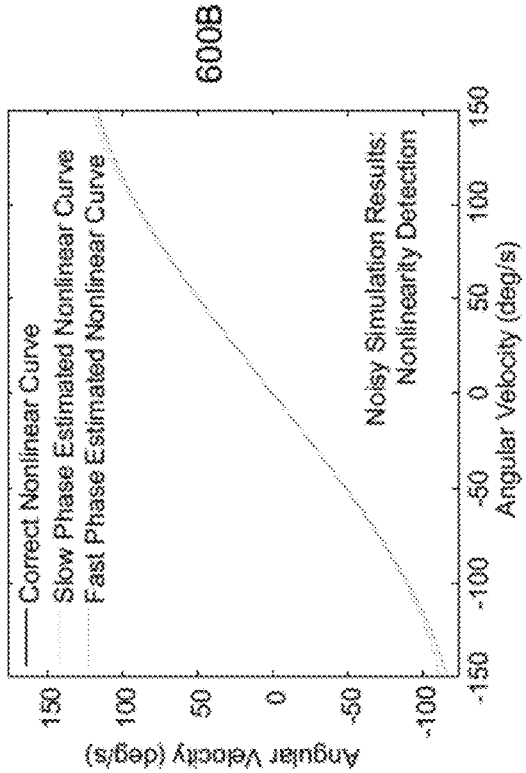
Figure 4B
Figure 5
Figure 6B

METHOD AND SYSTEM FOR AUTOMATICALLY CLASSIFYING AND IDENTIFYING VESTIBULO-OCULAR RESPONSES

CROSS-REFERENCE TO RELATED APPLICATIONS

This patent application claims the benefit of U.S. Provisional Patent Application U.S. 61/431,617 filed Jan. 11, 2011 entitled "Method and System for Automatically Classifying and Identifying Vestibulo-Ocular Responses."

FIELD OF THE INVENTION

The present invention relates to the vestibulo-ocular responses and more specifically to the processing of vestibulo-ocular responses for automatic classification/analysis, diagnosis and control.

BACKGROUND OF THE INVENTION

Stabilizing the visual system is a crucial issue for any sighted mobile creature, whether it is natural or artificial. The more immune the gaze of an animal or a robot is to various kinds of disturbances, e.g., those created by body or head movements when walking or flying, the less troublesome it will be for the visual system to carry out its many information processing tasks. This arises as typically the visual system, i.e. the human brain or microprocessor in robots, is too slow to process information if the images are slipping across the optical receptor, i.e. the human retina or charge coupled device (CCD) in robots, too rapidly—for the human brain this limit is as low as a few degrees per second, see for example G. Westheimer et al in "Visual acuity in the presence of retinal-image motion" (J Opt. Soc. Am., Vol. 65(7), pp 847-50).

Thus, while viewing a spatially-fixed target, the visual system must compensate for the motion of the head by turning the eyes in a direction opposite to the head. Another complication for vision in frontal-eyed animals is the development of a small area of the retina with a very high visual acuity, the fovea, which covers about 2 degrees of visual angle on average in humans. To get a clear view of the world, the visual control system must turn the eyes so that the image of the object is positioned reproducibly on the same region of the optical sensor whilst the determination of what is being imaged is made. For humans this means keeping the image centered on the fovea which is functionally similar to preventing image motion on a CCD sensor. Having two "eyes" is an added complication for both humans and robots, because the visual system must point both of them accurately enough that the object of regard falls on corresponding points of the two "sensors"; otherwise, double vision would occur. The movements of different body parts are controlled by striated muscles acting around joints. The movements of the eye are no exception, but they have special advantages not shared by skeletal muscles and joints, and so are considerably different.

Two reflexes within the human visual system are the optokinetic reflex, which allows the eye to follow objects in motion when the head remains stationary, and the vestibulo-ocular reflex (VOR) which stabilizes images on the retina during head movement by producing an eye movement in the direction opposite to head movement, thus preserving the image on the center of the visual field. In contrast "smooth pursuit movement" occurs where the eyes follow a moving object. Smooth pursuit tracking is less accurate than the vestibulo-ocular reflex, as it requires the brain to process incoming visual information and supply feedback to turn the eyes and, for a larger range of tracking, the head and/or body. Following an object moving at constant speed is relatively easy, though the eyes will often make saccadic jerks to keep up. The smooth pursuit movement can move the eye at up to 100°/s in adult humans.

With the vestibulo-ocular reflex (VOR) when the head moves to the right, the eyes move to the left, and vice versa and since slight head movement is present all the time, the VOR is very important for stabilizing vision in tasks such as reading. The human VOR system detects head movement and orientation in space without visual input and works even in total darkness or when the eyes are closed. However, in the presence of light, a re-fixation reflex is also added to the movement, where light sources in the periphery can cause the eyes to shift gaze direction under the control of the occipital lobe of the cerebral cortex.

Patients whose VOR is impaired find it difficult to read using print, because they cannot stabilize the eyes during small head tremors. Damage to the VOR system can cause such symptoms as vertigo, dizziness, blurred vision, and imbalance due to incorrect motions of the eyes relative to the head for humans. In robots poor stabilization may result in increased load on microprocessor analysis of the received images as well as imbalance and incorrect determination of movement in observed objects or body parts. Accordingly understanding the VOR in humans is important for:

diagnosis and treatment of patients, see for example R. Vaire "Diagnostic Value of Vestibulo-Ocular Reflex Parameters in the Detection and Characterization of Labyrinthine Lesions" (Otology & Neurotology, Vol. 27(4), pp. 535-541), J. M. Furman et al in "Vestibular Disorders: A Case Study Approach to Diagnosis and Treatment" (Oxford University Press, 2010), J. Edlow et al in "Diagnosis and initial management of cerebellar infarction" (The Lancet—Neurology, Vol. 7(10), pp 951-964), "Using Eye Movements as an Experimental Probe of Brain Function—A Symposium" (Elsevier, 2008);

providing visual prosthesis, often referred to as a bionic eye, for patients and presented for example in J. Loudin in "Optoelectronic retinal prosthesis: system design and performance" (J. Neural Eng., Vol. 4, pp S72-S84), C. Zhou et al in "Implantable Imaging System for Visual Prosthesis" (Artificial Organs, Vol. 34(6), pp 518-522) and L. Turicchia et al in "A Low-Power Imager and Compression Algorithms for a Brain-Machine Visual Prosthesis for the Blind" (Biosensing, Proc. SPIE, Volume 7035, pp. 703510-703510-13);

developing vision systems for robots, see for example S. Viollet et al in "A high speed gaze control system based on the Vestibulo-Ocular Reflex" (Robotics and Autonomous Systems, 50(4), pp 147-161), R. Kaushik et al "Implementation of Bio-Inspired Vestibulo-Ocular Reflex in a Quadrupedal Robot" (IEEE Conf. Robotics and Automation, 2007, pp 4861-4866), and A. Lenz et al in "An adaptive gaze stabilization controller inspired by the vestibulo-ocular reflex" (Bioinspiration and Biomimetics, Vol. 3, Iss. 3, pp. 035001).

The VOR has been studied mathematically for several decades, leading to many models in the literature, see for example O. J.-M. D Coenen et al in "Dynamical Model of Context Dependencies for the Vestibulo-Ocular Reflex" (Advances in Neural Information Processing Systems 8, MIT Press), S. Ramat et al in "Oculomotor responses to active head movements in darkness: formulation and testing of a mathematical model" (Ann N Y Acad Sci. 2001, pp 482-5.

2000) and S. Raphan et al in "The Vestibulo-Ocular Reflex in Three Dimensions" (Exp. Brain Res. Vol. 145, pp 1-27; Dieterich et al. 2003). Whilst these earlier models of the VOR provided insight into vestibular processes there remain many unresolved issues. The most important issue concerns data analysis and the "switched" nature of VOR responses. While VOR trajectories contain segments of fast and slow eye velocity, the prior art disregards the fast phases and links slow phase segments of eye velocity to estimate VOR dynamics.

Assuming correct pre-classification of nystagmus segments with these prior art approaches, then the clinical analysis of the VOR is limited to calculating the gain, time constant, and asymmetry of the envelope of the slow-phase response during step or harmonic rotations. As such this "envelope" approach results in the loss or misinterpretation of information, especially since the fast phases of nystagmus can also carry clinically relevant information. Furthermore, "envelope" based estimates are only valid (unbiased) for a continuous system while the VOR is clearly discontinuous in its response dynamics.

Indeed, the VOR falls into a class of systems called hybrid systems which exhibit multiple response strategies e.g. slow compensation and fast saccadic redirection for the human eye. It has been previously shown within the prior art that treating a hybrid system as a non-hybrid system leads to errors in identified reflex dynamics, which clearly impacts on diagnostic decisions and on interpretations of neural data. More recently improvements have been made to the estimation of VOR dynamics by pooling selected slow phase segments and separating the synergistic effects of fast phase end-points (i.e. the slow-phase initial conditions) from the common head-driven VOR dynamics. This improves the accuracy of estimated parameters, but again requires the correct pre-classification of the data.

Accordingly, an important issue for prior art mathematical analysis techniques is the requirement to classify the nystagmus segments before applying any analysis techniques, wherein this classification is preferably performed non-subjectively. Existing algorithms are based on ad-hoc measures and are not objective, since they require manual corrections especially for non-harmonic stimuli. Therefore it would be beneficial to overcome the above limitations by classification, i.e. segmentation of the data record into fast and slow phase pieces, and possibly artifacts or outliers, and identification concurrently and objectively as well as analyzing multi-input systems. It would be evident that improved analysis of the VOR in humans provides for:

improved diagnosis of patients;
improved treatment of patients;
improvements in performance of visual prosthesis for patients; and
improved performance of vision systems for mobile robotic systems.

Other aspects and features of the present invention will become apparent to those ordinarily skilled in the art upon review of the following description of specific embodiments of the invention in conjunction with the accompanying figures.

SUMMARY OF THE INVENTION

It is an objective of the present invention to provide a method and a system that can automatically process vestibulo-ocular responses and more specifically to allow the processing of vestibulo-ocular responses for automatic classification/analysis, diagnosis and control.

In accordance with an embodiment of the invention there is provided a method comprising:
(i) receiving input-output data relating to a characteristic of a system;
(ii) establishing with a microprocessor an estimate of at least one hybrid state of a plurality of hybrid states of the system;
(iii) establishing with the microprocessor in dependence upon at least the estimate a classification of the input-output data and an identification of a dynamic aspect of the system;
(iv) selecting at least one of classification of the input-output data and the identification of the dynamic aspect of the system in dependence upon errors of each with respect to the input-output data;
(v) generating a new estimate of the at least one hybrid state of a plurality of hybrid states of the system in dependence upon the selected at least one of classification of the input-output data and the identification of the dynamic aspect of the system;
(vi) iterating steps (iii), (iv) and (v) until a predetermined condition is satisfied;
(vii) detecting with the microprocessor at least one non-linearity of a plurality of non-linearities;
(viii) adjusting the determined parameters from the iterative analysis in dependence upon at least the non-linearity of the plurality of non-linearities; and
(ix) determining at least one of a static non-linearity parameter of a plurality of static non-linearity linear dynamic parameters and a linear dynamic parameter of a plurality of linear dynamic parameters.

In accordance with an embodiment of the invention there is provided a
a microprocessor;
a first non-transitory tangible computer readable medium for storing input-output data relating to a characteristic of a monitored system;
a non-transitory tangible computer readable medium encoding a computer program for execution by the microprocessor, the computer program comprising the steps of
(i) receiving input-output data relating to a characteristic of a system;
(ii) establishing with a microprocessor an estimate of at least one hybrid state of a plurality of hybrid states of the system;
(iii) establishing with the microprocessor in dependence upon at least the estimate a classification of the input-output data and an identification of a dynamic aspect of the system;
(iv) selecting at least one of classification of the input-output data and the identification of the dynamic aspect of the system in dependence upon errors of each with respect to the input-output data;
(v) generating a new estimate of the at least one hybrid state of a plurality of hybrid states of the system in dependence upon the selected at least one of classification of the input-output data and the identification of the dynamic aspect of the system;
(vi) iterating steps (iii), (iv) and (v) until a predetermined condition is satisfied;
(vii) detecting with the microprocessor at least one non-linearity of a plurality of non-linearities;
(viii) adjusting the determined parameters from the iterative analysis in dependence upon at least the non-linearity of the plurality of non-linearities; and
(ix) determining at least one of a static non-linearity parameter of a plurality of static non-linearity linear dynamic parameters and a linear dynamic parameter of a plurality of linear dynamic parameters.

In accordance with an embodiment of the invention there is provided a non-transitory tangible computer readable medium encoding a computer program for execution by the microprocessor, the computer program comprising the steps of:

(i) receiving input-output data relating to a characteristic of a system;
(ii) establishing with a microprocessor an estimate of at least one hybrid state of a plurality of hybrid states of the system;
(iii) establishing with the microprocessor in dependence upon at least the estimate a classification of the input-output data and an identification of a dynamic aspect of the system;
(iv) selecting at least one of classification of the input-output data and the identification of the dynamic aspect of the system in dependence upon errors of each with respect to the input-output data;
(v) generating a new estimate of the at least one hybrid state of a plurality of hybrid states of the system in dependence upon the selected at least one of classification of the input-output data and the identification of the dynamic aspect of the system;
(vi) iterating steps (iii), (iv) and (v) until a predetermined condition is satisfied;
(vii) detecting with the microprocessor at least one non-linearity of a plurality of non-linearities;
(viii) adjusting the determined parameters from the iterative analysis in dependence upon at least the non-linearity of the plurality of non-linearities; and
(ix) determining at least one of a static non-linearity parameter of a plurality of static non-linearity linear dynamic parameters and a linear dynamic parameter of a plurality of linear dynamic parameters.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIGS. 2A and 2B depict block diagrams of prior art VOR analysis approaches;

FIGS. 4A and 4B depict the results of processing according to an embodiment of the invention on noiseless simulated data;

FIG. 5 depicts a nonlinear curve estimated using current state of the art vestibulo-ocular reflex analysis methods;

FIGS. 6A and 6B depict the results of processing according to an embodiment of the invention on noisy simulated data;

DETAILED DESCRIPTION

The present invention is directed to vestibulo-ocular responses and more specifically to the processing of vestibulo-ocular responses for automatic classification/analysis, diagnosis and control within humans, animals and robotic systems.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims. While the invention is presented with respect to the angular VOR in the horizontal plane, it can be apply to any nystagmus or hybrid response, whether biological or engineered.

Figure 1A:
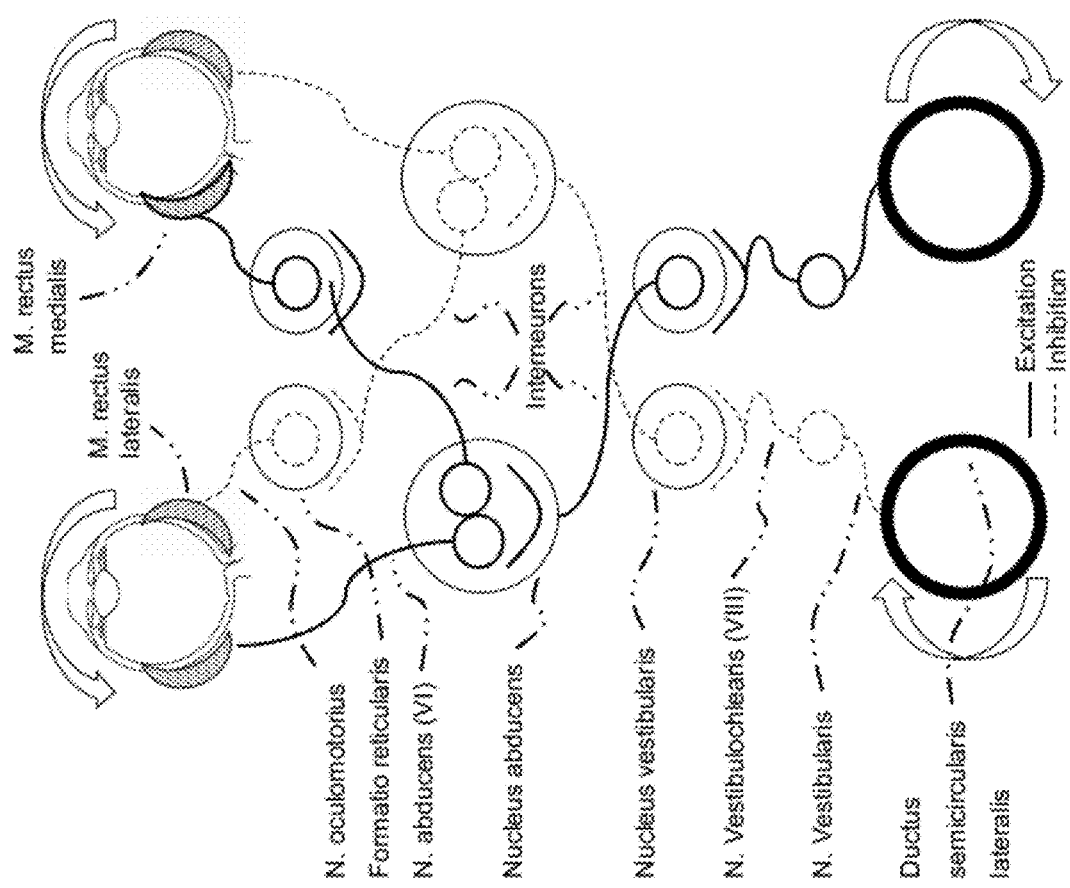
FIG. 1A depicts a schematic of the VOR linkage from the vestibular apparatus in the inner ear to the control of the ocular muscles wherein solid lines are excitatory (positive drive) pathways and dashed lines are inhibitory (negative drives) thereby producing a push-pull differential system.

Referring to FIG. 1A there is depicted a schematic of the VOR linkage from the vestibular apparatus in the inner ear to the control of the ocular muscles. The semicircular canals detect head rotation and drive the rotational VOR, whereas the otoliths, which are another structure in the saccule or utricle of the inner ear, detect head translation and drive the translational VOR. The semicircular canals in a human are three semicircular, interconnected tubes located inside each ear, being the horizontal semicircular canal (also known as the lateral semicircular canal), superior semicircular canal (also known as the anterior semicircular canal), and the posterior semicircular canal. The canals are aligned approximately orthogonally to one another. The horizontal canal is aligned roughly horizontally in the erect head. The superior and posterior canals are aligned roughly at a 45-degree angle to a vertical plane through the nose and the back of the human skull. Thus, the horizontal canal detects horizontal head movements around a vertical axis (such as when doing a pirouette), while the superior and posterior canals detect vertical head movements around axes lying in the horizontal plane.

The main "direct path" neural circuit for the horizontal rotational VOR is fairly simple. It starts in the vestibular system, where the semicircular canals get activated by head rotation and send their impulses via the vestibular nerve (cranial nerve VIII) through Scarpa's ganglion and end in the vestibular nuclei in the brainstem. From these nuclei, fibers cross to the contralateral cranial nerve VI nucleus (abducens nucleus). There they synapse with 2 additional pathways. One pathway projects directly to the lateral rectus of eye via the abducens nerve. Another nerve tract projects from the abducens nucleus by the medial longitudinal fasciculus to the oculomotor nuclei, which contain motorneurons that drive eye muscle activity, specifically activating the medial rectus muscles of the eye through the oculomotor nerve. Similar pathways exist for the vertical and torsional components of the VOR. As depicted in FIG. 1A rotation in one direction inhibits one direct neural path and excites the other and conversely rotation in the other direction results in the opposite neural path excitation and inhibition.

In addition to these direct pathways, which drive the velocity of eye rotation, there is an indirect pathway that builds up the position signal needed to prevent the eye from rolling back to center when the head stops moving. This pathway is particularly important when the head is moving slowly, because here position signals dominate over velocity signals. This is accomplished in the brain by mathematically filtering the velocity signal and then sending the resulting position signal back to vestibular nuclei. This feedback loop acts as a "neural integrator" for horizontal eye position by interconnecting vestibular nuclei with the nucleus prepositus hypoglossi in the medulla. Similar integration for vertical and torsional eye positions involves instead the interstitial nucleus of Cajal in the midbrain. The networks of neural integrators are shared by all reflexes generating eye movements, for example also generating eye position for any movements such as saccades and smooth pursuit.

The classification/identification of VOR responses can be translated into a multivariate optimization problem. Within the prior art, a classification step always precedes any analysis of nystagmus responses. These prior art methods rely on a priori assumptions, e.g. forcing the slow phase eye velocity segments to belong to an envelope resembling the trajectory profile of head velocity, or segregation according to a priori criteria on eye trajectories such as direction relative to the head and velocity thresholds, or more recently classification according to reduced model predictions. At present these prior art techniques do not provide an easy-to-use tool for researchers and clinicians in view of the complexities of this system. Accordingly analysis is still dependent on experts who must review and edit the segmentation results because of over-simplifying apriori conditions.

In summary, the classification/identification of VOR responses appears to be a chicken and egg problem. If one is provided with perfect classification of the data, algorithms exist to optimally identify system dynamics. Inversely, if one is provided with perfect knowledge of mode dynamics, optimal classification can be achieved by comparing the responses at each point in the data record with the provided model predictions. Therefore, iterating between classification and identification could improve the overall results. However, obtaining one requires the other.

Figure 1B:
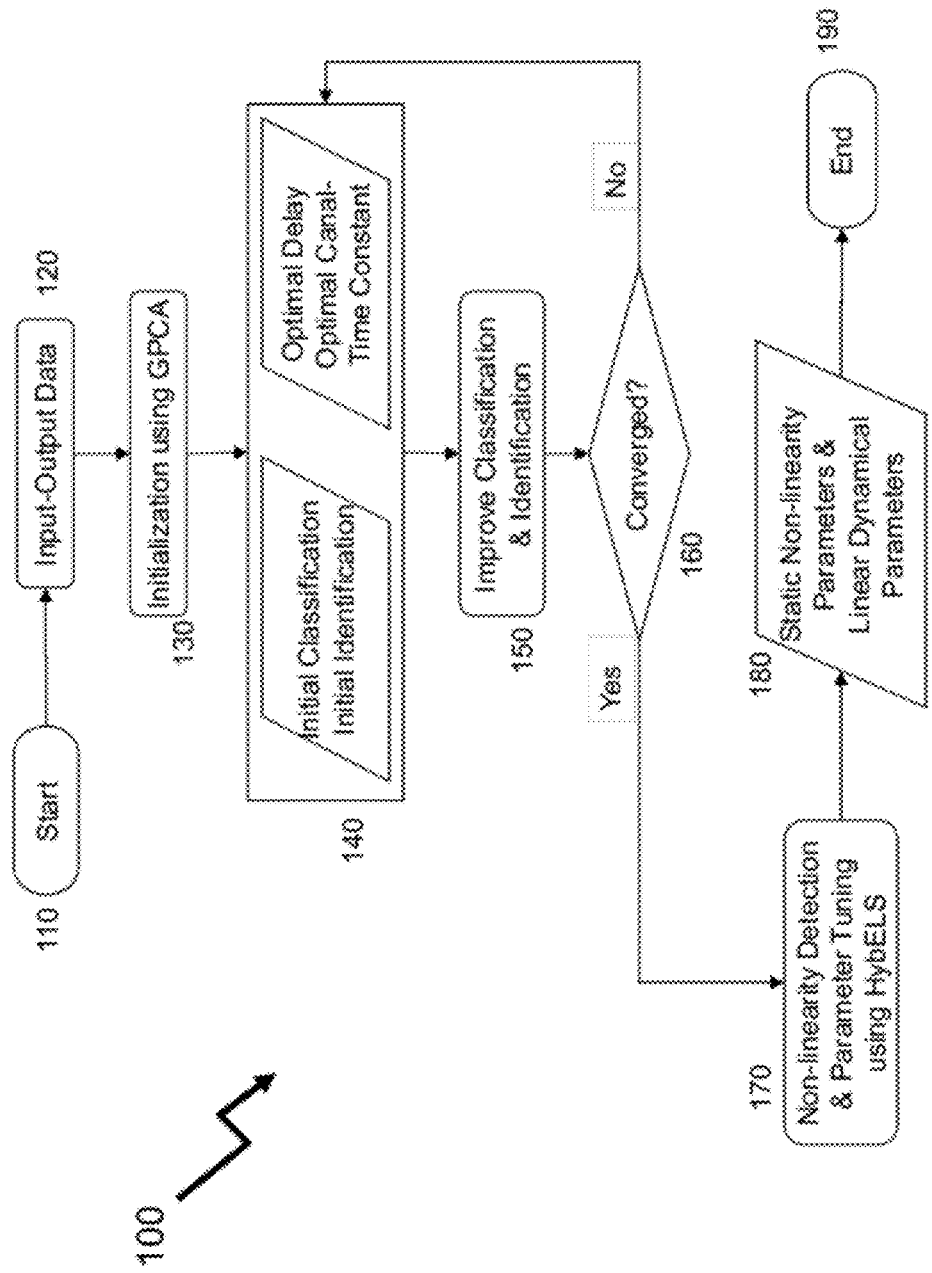
FIG. 1B depicts a flowchart for automatic nystagmus processing providing classification and analysis of vestibulo-ocular reflex data according to an embodiment of the invention.

Referring to FIG. 1B there is presented a process flow 100 according to an embodiment of the invention. The process starts in step 110 and proceeds to step 120 wherein input and output data are received. From this an "initial estimate" is required of the segment (slow versus. fast) classification in the data record. This is achieved in step 130 through use of a Generalized Principal Component Analysis (GPCA) methodology. GPCA is an unsupervised subspace segmentation method which finds an algebro-geometric solution to the problem of segmenting a number of subspaces of potentially varying dimensions and their normals from sample data points. GPCA has been shown to provide a good initialization to iterative techniques such as K-subspaces and Expectation Maximization.

Assuming linearity and time-invariance, the input-output equation of the hybrid system in mode $m_k$ in the Laplace domain is written as:

$$Y(s) = H_k(s)U(s) \tag{1}$$

or in the z-domain as:

$$Y(s) = H(z)U(z) = \frac{(a_0 + a_1 z^{-1} + \ldots + a_r z^{-r})U(z)}{(1 + b_1 z^{-1} + \ldots + b_q z^{-q})} \tag{2}$$

Since the responses are continuous, the discrete-time input-output equation for a data segment of length L in mode $m_k$, in the noise-free case can be written as:

$$y(n) = \sum_{i=0}^{r} a_i u(n-1) - \sum_{j=1}^{q} b_j y(n-j), \tag{3}$$

$n = j_1, \ldots, j_L$
$y(i), u(i)$ for all $i < 0$ substituted from the previous segment
or $$\sum_{i=0}^{r} a_i u(n-1) - \sum_{j=1}^{q} b_j y(n-j) - y(n) = 0, \tag{4}$$

$n = j_1, \ldots, j_L$

This translates into:

$$[u(n) \ldots u(n-r)y(n-1) \ldots y(n-q)y(n)] \cdot \vec{\theta}_{m_k} = 0, n = j_1, \ldots, j_L \tag{5}$$

where $\vec{\theta}_{m_k}$ is the parameter vector corresponding to the mode $m_k$.

If the regressor vector $[u(n) \ldots u(n-r)y(n-1) \ldots y(n-q)y(n)]$ is defined as $\vec{R}_n$, the above equation would mean that the data points corresponding to mode $m_k$ lie on a hyper-plane in $R^{r+q+2}$. Repeating the same procedure, it is possible to write equations (1) to (5) for other modes of the system as well. Therefore, in the case of the VOR where there are two modes $m_1$ and $m_2$, for all the data record, the data points lie on either of the hyper-planes:

$$\vec{R}(n)^T \cdot \vec{\theta}_{m_1} = 0 \tag{6}$$

or $$\vec{R}(n)^T \cdot \vec{\theta}_{m_2} = 0 \tag{7}$$

Hence, all data points in the record satisfy:

$$(\vec{R}(n)^T \cdot \vec{\theta}_{m_2})(\vec{R}(n)^T \cdot \vec{\theta}_{m_2}) = 0 \tag{8}$$

A proper embedding is used to map these hyper-planes to a single hyper-plane in a higher dimensional space. One such embedding is called the Veronese map ("Algebraic Geometry, A First Course", Springer-Verlag, 1992). Using this map will result in:

$$V_2([u(n) \ldots u(n-r)y(n-1) \ldots y(n-q)y(n)]) \cdot \vec{\theta}_{emb} = 0$$
for all $n=1,\ldots,T$ (9)

where T is the length of the whole data record. The variable $\vec{\theta}_{emb}$ is found using regression and then map it back to the original space to attain the classification and subspace normal vectors $\vec{\theta}_{m_1}$ and $\vec{\theta}_{m_2}$. This procedure can be performed for hybrid systems with more than two modes as well.

It is well-known that there is a delay of approximately 5-7 ms associated with the VOR for primates and man. Therefore, before mapping $\vec{\theta}_{emb}$ back to the original low-dimensional space to solve for subspace normal vectors, a search for possible input transport delays is done by substituting in (9), delayed versions of the input and searching for the one that yields minimum root mean squared regression error, regardless of the estimated parameter vector:

$$d_0 = \operatorname*{argmin}_{d} \sqrt{\left(\frac{1}{T-D}\sum_{n=D+1}^{T}\left(V_2([u(n) \ldots u(n-r)y(n-1) \ldots y(n-q)y(n)]) \cdot \vec{\theta}_{emb}\right)^2\right)},$$ (10)

where D is the maximum delay value. With the optimal delay value, we replace u(n) with $u(n-d_0)$ for the rest of the analysis, and proceed with the canal time constant detection, followed by the GPCA to obtain the classification and parameter estimation. Since the delay of the VOR is reported to be approximately 5-7 ms for primates and man, the search is constrained for the estimated delay to the range of 0 to 20 ms.

After detecting the input delay, the SCC time constant is determined. SCCs sense the head velocity during both fast and slow phases, and are a non-switching component of the VOR system. In order to study the dynamics of the switching components of the system, it is first required to estimate the dynamics of the semi-circular canal (SCC). In the bandwidth of normal head movement, SCCs are high-pass filters of head velocity with a first order transfer function approximation of the form $$\frac{T_C \cdot s}{T_C \cdot s + 1},$$

where $T_C$ is the SCC time constant. Therefore only $T_C$ is required to identify the dynamics of the SCCs.

To do this, the experimental input signal is filtered through a unity gain high pass filter with a variable time constant. This filtered input signal is used, associated mode dynamics are identified, and the goodness of fit for VOR identification with different time constants in the high pass filter is compared. Just like the delay detection step, the time constant which results in the minimum fitting error is saved but the other parameter estimates are discarded. The optimal SCC time constant is thus taken to be $$T_{C_0} = \operatorname*{argmin}_{TC} \sqrt{\left(\frac{1}{T-D}\sum_{n=D+1}^{T}\left(V_2([u*h_{TC}(n) \ldots u*h_{TC}(n-r)y(n-1) \ldots y(n-q)y(n)]) \cdot \vec{\theta}_{emb}\right)^2\right)},$$ (11)

where $h_{TC}$ is the impulse response function of a unity gain high pass filter with a time constant of $T_C$. Once again, we replace u(n) with $(u*h_{TC_0})(n)$ (the convolution of the input with the estimated canal impulse response function) for the rest of the analysis. Since the dominant cupula time constant is approximately 5-7 s in primates, and man, and vestibular responses can exhibit 12-15 s decay patterns within the velocity storage of the neural circuits, the search for the vestibular (sensory) time constant is constrained between 2 s and 20 s.

GPCA is a powerful unsupervised tool for simultaneous classification and identification of hybrid systems in noiseless and low dimensional conditions. However, its performance can deteriorate significantly in the presence of noise, or when model orders increase. This limitation is mitigated by implementing GPCA only for initialization, and then correct for possible classification errors by minimizing the (1-step) prediction errors iteratively using repeated classification/identification steps.

Note that in the presence of noise, considering an ARMAX (AutoRegressive Moving Average with eXogenous input) structure for the system, equation (3) changes to:

$$z(n) = \sum_{i=0}^{r} a_i u(n-1) - \sum_{j=1}^{q} b_j z(n-j) + \sum_{p=0}^{l} c_p e(n-p),$$ (12)

where z(n) is the observed noisy output and e(n) is the additive noise. The regressors also change in turn from [u (n) . . . u(n−r)y(n−1) . . . y(n−q)y(n)] to [u(n) . . . u(n−r)z(n−1) . . . z(n−q)z(n)], and equations (6) and (7) change to:

$$\vec{R}(n)^T \cdot \vec{\theta}_{m_1} = \sum_{p=0}^{l} c_p e(n-p)$$ (13)

or $$\vec{R}(n)^T \cdot \vec{\theta}_{m_2} = \sum_{p=0}^{l} c_p e(n-p).$$ (14)

Equations (13) and (14) yield the output prediction errors from the currently identified models. Therefore, estimating the parameter vectors $\vec{\theta}_{m_2}$ and $\vec{\theta}_{m_2}$ translates into finding the parameter vectors that minimize prediction errors. This can be formulated into an optimization problem by defining the cost function as:

$$f\left(\mu(n), \{\vec{\theta}_{m_1}, \vec{\theta}_{m_2}\}\right) = \sum_{n=1}^{T} [z(n) - pred(z(n))]^2 \qquad (15)$$

$$= \sum_{n=1}^{T} \left\{ \left[(2-\mu(n))\left(\vec{R}(n)^T \cdot \vec{\theta}_{m_1}\right)\right]^2 + \left[(\mu(n)-1)\left(\vec{R}(n)^T \cdot \vec{\theta}_{m_2}\right)\right] \right\}$$

where $\mu(n)$ is a membership function which assigns a mode to each data point:

$$\mu(n) = \begin{cases} 1 & \text{if the } n^{th} \text{ data point is classified in } m_1 \\ 2 & \text{if the } n^{th} \text{ data point is classified in } m_2 \end{cases} \qquad (16)$$

Our goal is to find values of $\mu(n)$, $\{\vec{\theta}_{m_1}, \vec{\theta}_{m_2}\}$ which minimize f. The membership function $\mu(n)$ would then represent the best classification of the data, while $\{\vec{\theta}_{m_1}, \vec{\theta}_{m_2}\}$ would represent the identified parameters for the two modes of the system. Since these parameters are interdependent, we cannot find a closed form solution for this optimization problem. Therefore, we optimize f only with respect to one set of parameters at a time:

$$\frac{\partial f}{\partial \{\vec{\theta}_{m_1}, \vec{\theta}_{m_2}\}} = 0, \text{ given } \mu(n) \qquad (17)$$

and $$\frac{\partial f}{\partial \mu(n)} = 0, \text{ given } \{\vec{\theta}_{m_1}, \vec{\theta}_{m_2}\} \qquad (18)$$

The solution to these equations is given by $$(2-\mu(n))^2\left(\vec{R}(n)^T \cdot \vec{\theta}_{m_1}\right) + (\mu(n)-1)^2\left(\vec{R}(n)^T \cdot \vec{\theta}_{m_2}\right) = 0, \qquad (19)$$
$$n = 1, \ldots, T$$

and $$\mu(n) = \frac{2\vec{R}(n)^T \cdot \vec{\theta}_{m_1} + \vec{R}(n)^T \cdot \vec{\theta}_{m_2}}{\vec{R}(n)^T \cdot \vec{\theta}_{m_1} + \vec{R}(n)^T \cdot \vec{\theta}_{m_2}} \qquad (20)$$
$$n = 1, \ldots, T$$

The first solution, when $\mu(n)$ is known and $\{\vec{\theta}_{m_1}, \vec{\theta}_{m_2}\}$ is sought after, can be solved with a least squares method. However, for the hybrid case, some modifications need to be made, giving rise to a Hybrid Least Squares method. The second solution, where now $\{\vec{\theta}_{m_1}, \vec{\theta}_{m_2}\}$ is known and $\mu(n)$ is sought after, is achieved by assigning each data point to the mode that results in the smallest (1-step) prediction error from the current identified dynamics; in other words, $\mu(n)$ is 2 when the prediction error assuming $m_2$, $\vec{R}(n)^{T} \cdot \vec{\theta}_{m_2}$, is smaller than the prediction error assuming $m_1$, or $\vec{R}(n)^{T} \cdot \vec{\theta}_{m_1}$. Similarly, $\mu(n)$ is 1 when the prediction error assuming $m_1$, $\vec{R}(n)^{T} \cdot \vec{\theta}_{m_1}$, is smaller than the prediction error assuming $m_2$, $\vec{R}(n)^{T} \cdot \vec{\theta}_{m_2}$.

In summary, the methodology presented within FIG. 1B is to minimize the cost function, the initial classification and parameters given by GPCA are used in step 140, and then optimized iteratively using equations (19) and (20) in step 150. Given the identified parameters, at every point in the data record, the method compares the errors given by the two models, and chooses the model resulting in the least error as the correct one. This results in a new classification. Using this updated classification, estimates are produced of the parameters of the two modes of the system, improving the identification. Iterations continue until convergence of the residuals occurs, as determined in step 160. At each iteration, in order to avoid the biasing effects of outliers or artifacts, the points from the data record whose prediction errors are greater than 2 standard deviations (STDs) of the residuals are removed. However, each pass re-evaluates all prediction errors and a new associated set of outliers, in other words they are not accumulated.

Following the steps above and determination of convergence in step 160, it can be assumed that the classification of data segments is now complete. It is known that there are nonlinearities associated with the VOR, especially in abnormal cases. Therefore, with the classification vector fixed, a Hybrid Extended Least Square (HybELS) method introduced by Ghoreyshi and Galiana, see A. Ghoreyshi and H. L. Galiana in "A Hybrid Extended Least Squares method (HybELS) for Vestibulo-Ocular Reflex identification" (Conf. Proc. IEEE Eng. Med. Biol. Soc., 2009, pp 4958-4961), is then used to fine-tune the estimated parameters (model orders) and to detect possible non-linearities. This nonlinearity detection is postponed until the classification is finalized, because incorporating the nonlinearities in the model from the beginning increases the complexity of the model, and affects the correct convergence of the classification. This non-linearity detection is performed in two steps, initially in step 170 non-linearity detection and parameter tuning using the HybELS is performed and then in step 180 static non-linearity parameters and linear dynamical parameters are established wherein the process stops in step 190.

A NARMAX (Nonlinear ARMAX) framework to model nonlinearities. Assuming a static nonlinearity of the polynomial form:

$$w(n) = \sum_{k=1}^{N} a_k u^k(n) \qquad (21)$$

which precedes the linear time-invariant system described above, representing central premotor dynamics according to equation (12):

$$z(n) = \sum_{i=0}^{r} a_i w(n-i) - \sum_{j=1}^{q} b_j z(n-j) + \sum_{p=0}^{l} c_p e(n-p). \qquad (22)$$

Replacing for w(n) from (21) yields:

$$z(n) = \sum_{i=0}^{r}\sum_{k=1}^{N} a_{ik} u^k(n-1) - \sum_{j=1}^{q} b_j z(n-j) + \sum_{p=0}^{l} c_p e(n-p) \quad (23)$$

To account for nonlinearities a modified HybELS, which the inventors refer to as GNL-HybELS, is applied by changing the regressor vectors accordingly and this can be used to fine-tune the parameter estimation for the dynamics of the system, and to estimate coefficients of the nonlinearity. The outliers are again discarded by removing the data points with extreme residuals, and re-estimating the parameters as above, to prevent the outliers from biasing the results.

It has been shown in the prior art that conventional VOR analysis methods which use the envelope of eye velocity yield biased results. In order to compare the performance of the current state-of-the-art envelope method with GNL-HybELS, the envelope method was tested on noise-free simulated data, estimating the canal time constant, and a static nonlinearity. In this envelope method, the assumption is that the eye velocity is a high-pass filtered version of the head velocity in the slow phase mode, sampled through slow phase intervals. Therefore, the plot of eye velocity data points during slow phases versus head velocity would appear as an ellipse, due to the phase difference between the signals. If the head velocity signal is high-pass filtered by the correct transfer function, or shifted in time by the right amount in sinusoidal cases, the loop will collapse onto a line or curve. Therefore, to find the correct canal time constant, one would look for the time shift that best reduces the elliptical pattern into a single curve. If the VOR seems linear, the slope of the resulting line represents the gain of the VOR, while the shape of a resulting curve describes the static nonlinearity of the system.

Note that even in optimal cases, this method is incapable of estimating the hybrid dynamics of the system, and identifies only one global time constant (a global vestibular time constant) at best. FIGS. 2A and 2B demonstrate the system structures identified by GNL-HybELS method 200 and the envelope method 250 respectively. The conventional head position or velocity signals are mainly sinusoids, steps, and ramps. However, it is known that these signals are far from optimal for system identification purposes. Such signals are band-limited, and therefore, would not allow for correct estimation of dynamical parameters in a system with potentially more than one time constant. Furthermore, when pure sinusoids are used as input signals, any transmission delay cannot be differentiated from a phase shift due to dynamics (poles), since in steady-state, both processes will appear as delays in responses.

To improve the capacity to identify VOR dynamics, a richer head trajectory profile that covers the bandwidth of the VOR has been designed by the inventors, which is limited to about 1 Hz. Hence the slow phase segments are expected to have a bandwidth of 1-3 Hz depending on linearity, while fast phases have a bandwidth closer to 30 Hz due to smaller poles and switching. A low-pass filtered white noise signal with a 5 Hz bandwidth, is compared to ⅙ Hz sinusoidal signals as the head position input (Note that the switching increases the effective bandwidth of the input, because of the existence of initial conditions at every switching instance). An acceleration limitation of 350 deg/s$^2$ for a rotating chair was considered when designing the input. The sampling rate could be selected between 100 Hz and 1000 Hz, however, a low-pass filter was applied to the data at 35 Hz (digital filtering) and then decimated to 100-200 Hz. Using experimentally observed data on stimuli and eye responses to define a realistic switching pattern, this pattern and input profile were then used in simulation runs to make them as 'natural' and pertinent as possible, see FIG. 3.

In order to validate this method, it was first tested on simulated data where the correct classification and identification parameters are available and a previously established model of the oculomotor system generated the simulated VOR data. Correct identification also requires that the stimulus have a sufficiently high bandwidth to cover the expected system dynamics. Hence we use a pseudo-random head velocity profile. In this setting, the parameters of system dynamics as well as the switching instances between fast and slow modes are known, and precise evaluation of the performance of our algorithm in terms of identification and classification, can be done.

Figure 3:
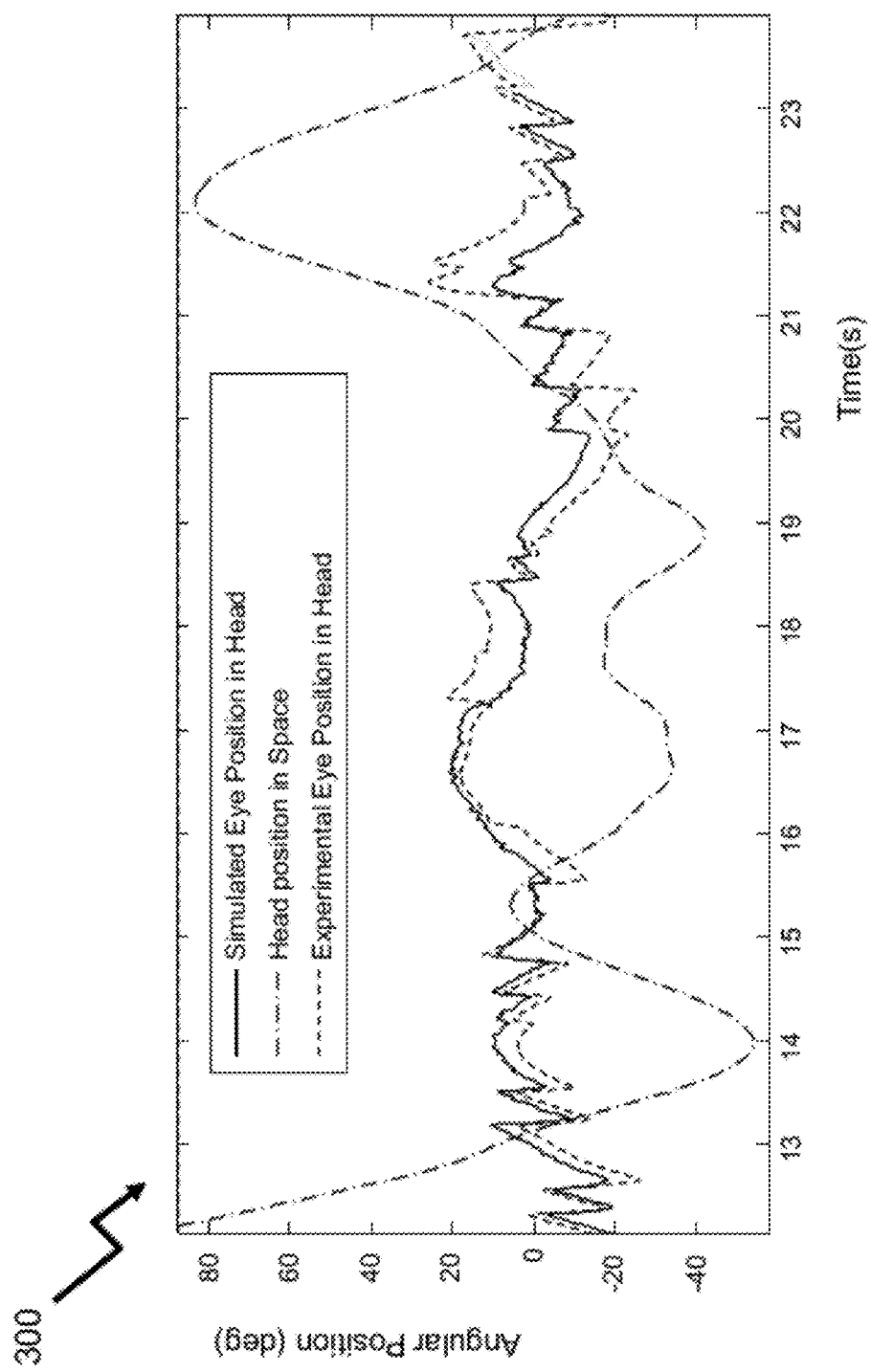
FIG. 3 depicts a simulated VOR data sample for head and eye movement.

The same head input as the experimental head input was selected for the simulations to be as close to real conditions as possible. FIG. 3 in graph 300 depicts a sample of both the simulated and experimental eye positions, as well as the head position. The delay was chosen to be 10 ms and the nonlinearity to be of third order: $p(x) = x + 0.00001x^3$. The system dynamics, filter 210 of FIG. 2A, were made first order with a transfer function (eye position versus head velocity) of $$\frac{-.72}{s + .15}$$

in the slow phase mode and a transfer function of $$\frac{4.0}{s + 26}$$

in the fast phase mode. The canal time constant was 15 s, the sampling rate was 100 Hz, and the record length was 30 s.

Figure 4A:
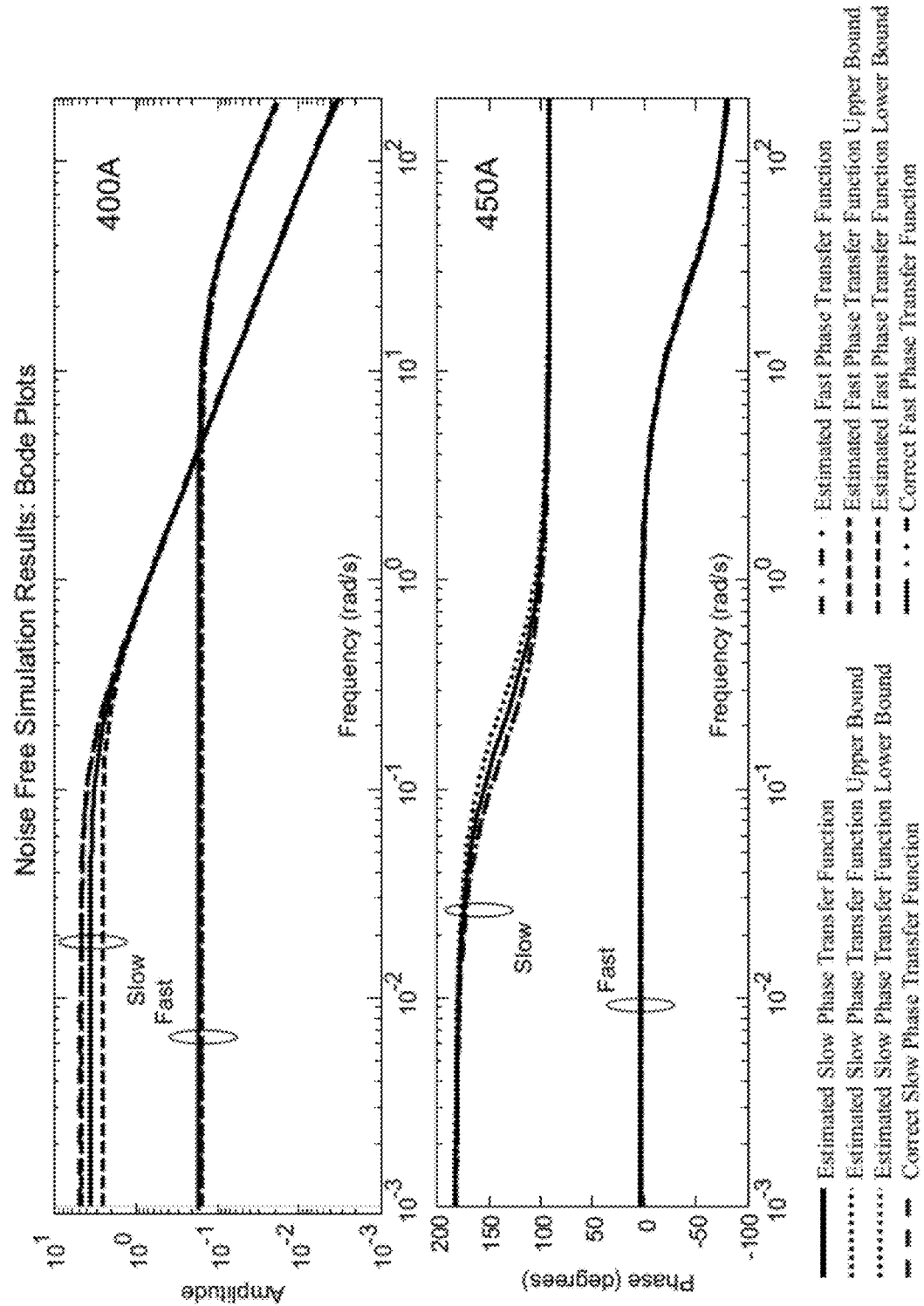

First, results in the absence of noise are provided in FIGS. 4A and 4B, showing estimates from GNL-HybELS for the nonlinearity in FIG. 4B and the LTI system's dynamics in terms of the transfer function for eye position versus head velocity in FIG. 4A, with 1 standard deviation (STD) error bounds. This method produced an estimated canal time constant of 15 s, and an estimated gain of −0.72±0.001. Results are summarized quantitatively below in Table 1.

TABLE 1

Noise-Free and Noisy GNL-HybELS Analysis Results

| | Noise-Free | Noisy (1 deg STD) |
|---|---|---|
| Delay [10 ms] | 10 ms | 10 ms |
| Canal Time Constant [15 s] | 15 s | 13 s |
| RMS Prediction Error | .18 deg | .87 deg |
| Classification Error | 2.4% | 6.2% |
| Estimated Slow Phase Linear Coefficient [1] ± STD | 1.0 ± −9.9e−4 | 1.0 ± 6.6e−3 |
| Estimated Slow Phase Cubic Coefficient [1e−5] ± STD | (−.99 ± .072)e−5 | (−1.1 ± .13)e−5 |
| Estimated Fast Phase Linear Coefficient [1] ± STD | 1.0 ± 3.3e−3 | 1.0 ± 5.7e−3 |
| Estimated Fast Phase Cubic Coefficient [1e−5] ± STD | (−.91 ± .12)e−5 | (−.94 ± .17)e−5 |

In order to compare GNL-HybELS with the classic envelope method, the latter was also applied to the same noise-free simulated data, to find its estimate of the canal time constant, gain, and the nonlinearity. The envelope method resulted in an estimated canal time constant of 19 s, and an estimated gain of −0.69±0.003, whereas the correct canal time constant used in the simulation was 15 s, and the correct gain −0.72. This result confirms previous studies that the envelope method yields biased estimates. Clearly, it would be evident that since simulated data was used, it is known when the switching between fast and slow phases occurred. Therefore, perfect classification of the data was available which is impossible to achieve with experimental data. The result of the envelope method in the estimation of the nonlinearity is shown in FIG. 5. Even with perfect classification of the data at hand, the envelope method fails to correctly identify the canal time constant, gain, and the nonlinearity in the noise-free case. In addition, it does not provide for potential dynamics at the premotor level that may not comply with the assumption of a pure integrator.

It is also important to mention that the estimated time constant and nonlinearity using the envelope method also depend on the switching pattern between slow and fast phase modes, which alters fast phase end points. Hence results of analysis on experimental data cannot be expected to be robust or repeatable.

Figure 6A:
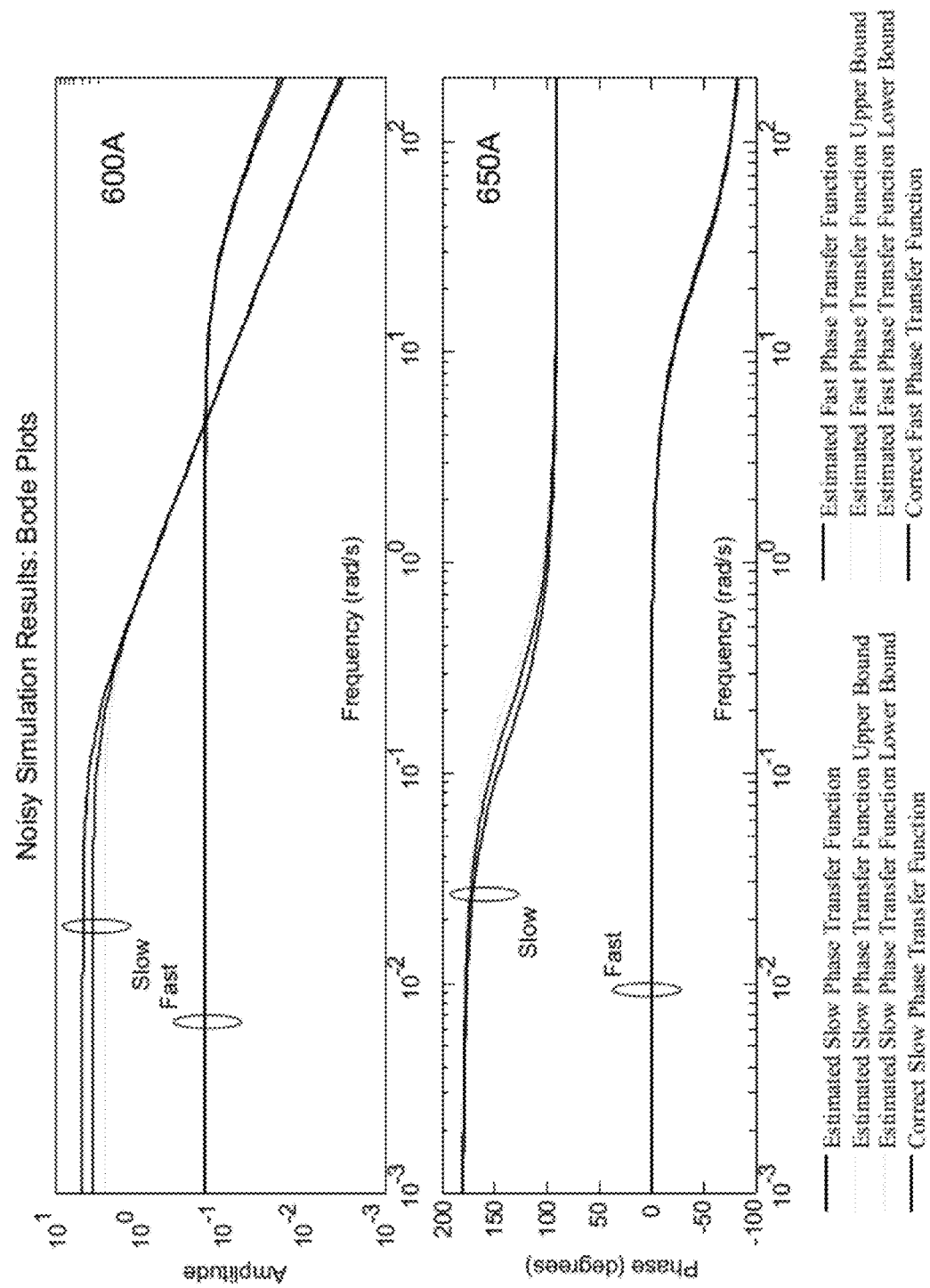

To test the method of the inventors in noisy conditions, Gaussian white noise of 1 deg standard deviation was added to the simulation output and re-evaluated allowing the performance of the invention to be determined. The results in delay detection and nonlinearity representing the estimation of the LTI system's dynamics are demonstrated in FIGS. 6A and 6B respectively. The quantitative errors are listed in Table 1, and the estimated parameters are very close to the nominal values, with small standard deviations.

Figure 7:
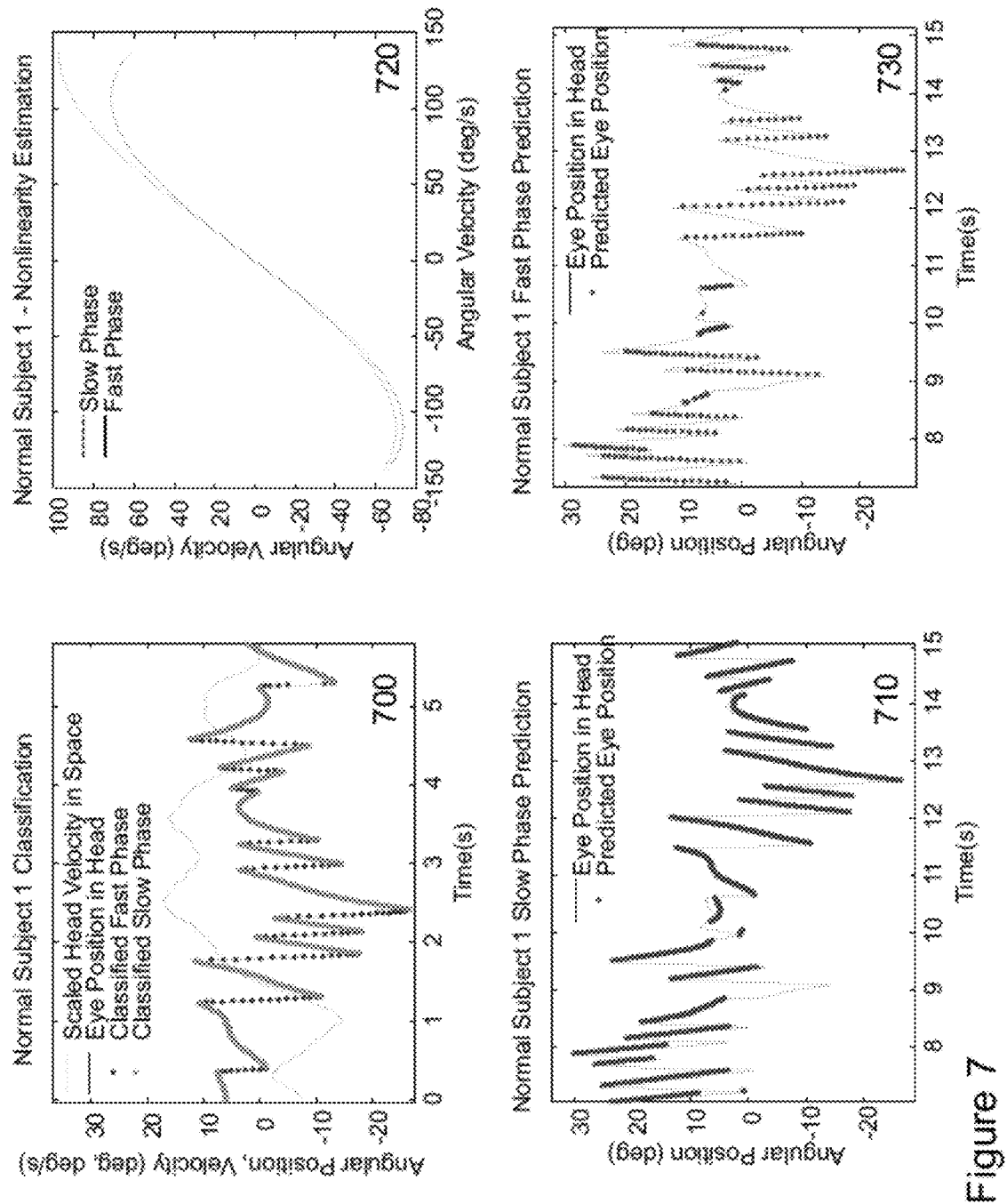
FIG. 7 depict the results of processed classification and identification according to an embodiment of the invention on data from a normal subject.

Most classification errors are located over a few points at the switching boundaries between slow and fast phases, i.e. at the edges of the segments rather than the middle of them. FIG. 7 depicts examples of classified data in an experimental data record for a human subject with classification in first graph 700, slow phase prediction in second graph 710, nonlinearity estimation in third graph 720, and fast phase prediction in fourth graph 730. Therefore, the effect of the few misclassified data points on the estimation of system parameters is minimal. Furthermore, it is mainly the fast phase edge data points that are misclassified as belonging to the slow phase; as a result, the estimation of fast phase dynamics is the most accurate, but the slow phase dynamics are still very close to the correct dynamics as evident in FIG. 6A.

It would be evident to one skilled in the art that the GPCA's accuracy deteriorates significantly with noise. On the noise-free simulation, GPCA alone resulted in 6.9% classification error, and 3.7 deg of prediction error. However, in the noisy case, the classification error increased to 46%, and the prediction error to 1.6e05 deg, which means that GPCA by itself basically fails in the noisy case. This is why the method according to embodiments of the invention only uses GPCA for initialization, and fine-tunes the results using the steps that follow GPCA.

The performance of the invention was also evaluation on experimental data from 6 normal subjects and 6 patients. Since no ground truth is available for the correct classification and identification exists, root mean squared (rms) prediction errors were used as measures of the accuracy of the results. The order of the estimated static nonlinearity was again 3. The results of the analyses are listed below in Table 2 for normal subjects and Table 3 for patients.

Figure 8:
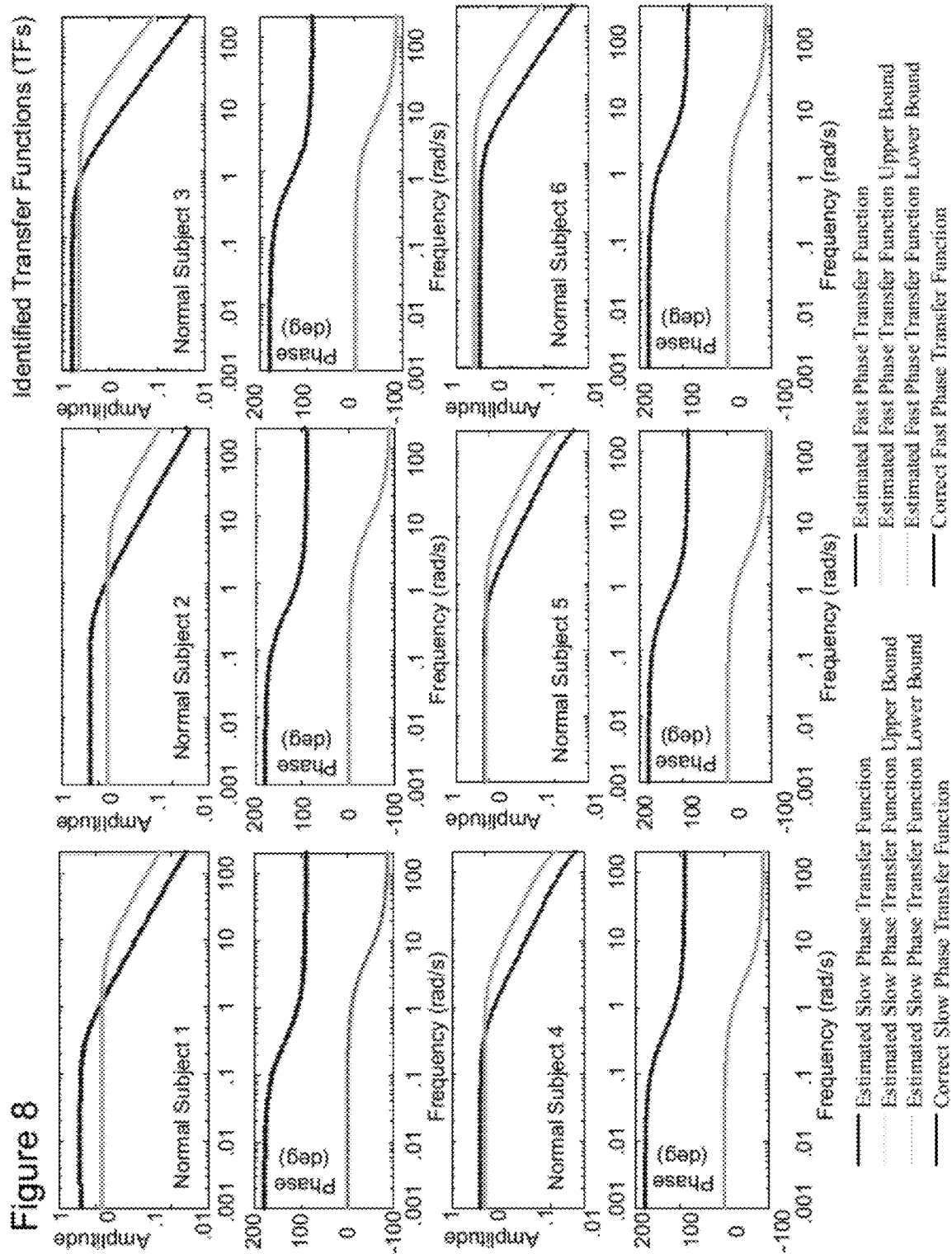
FIG. 8 depict the results of processing according to an embodiment of the invention on data from 6 normal subjects showing the identified transfer functions with one standard deviation error.
Figure 9:
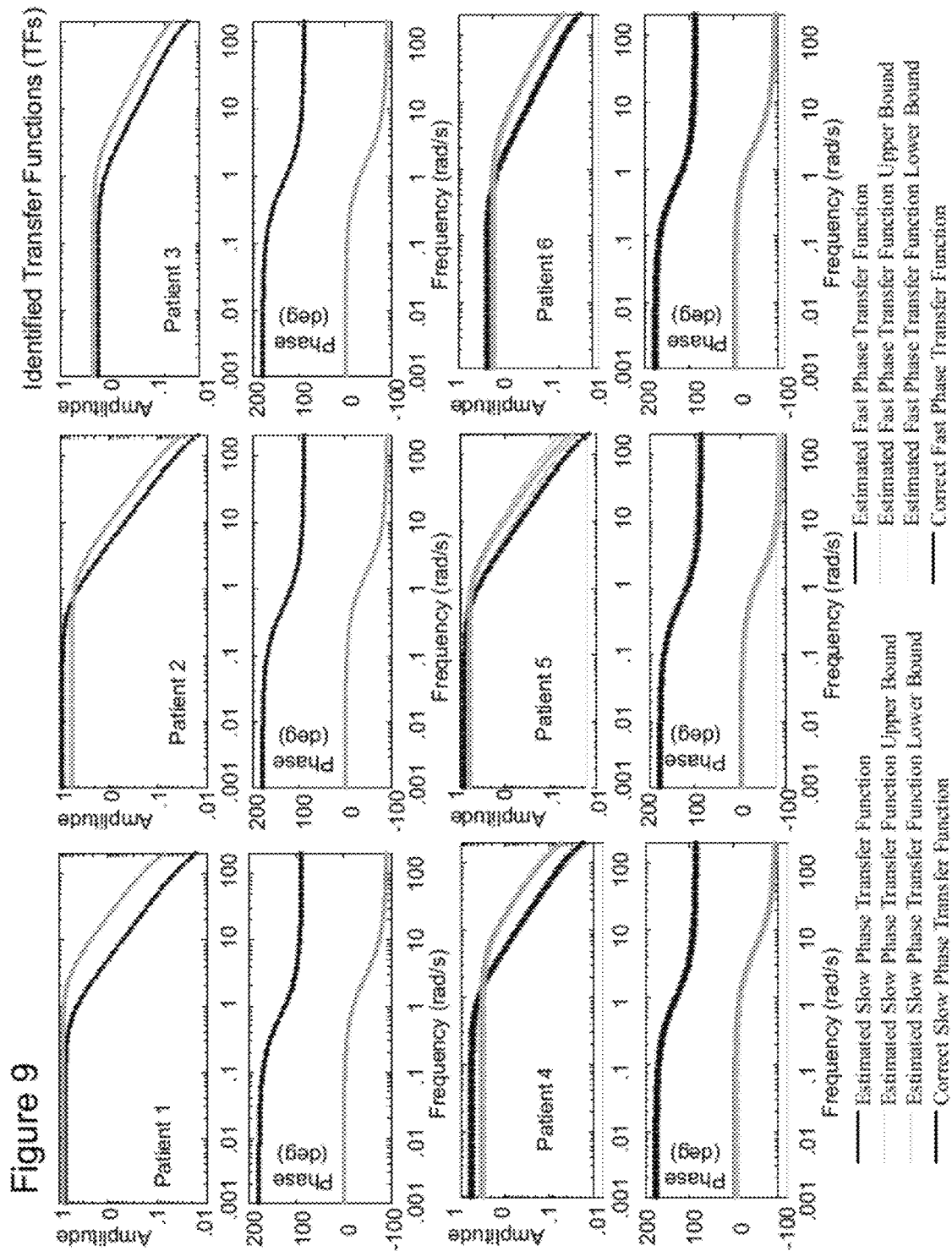
FIG. 9 depict the results of processing according to an embodiment of the invention on data from 6 patients showing the identified transfer functions with one standard deviation error.
Figure 10:
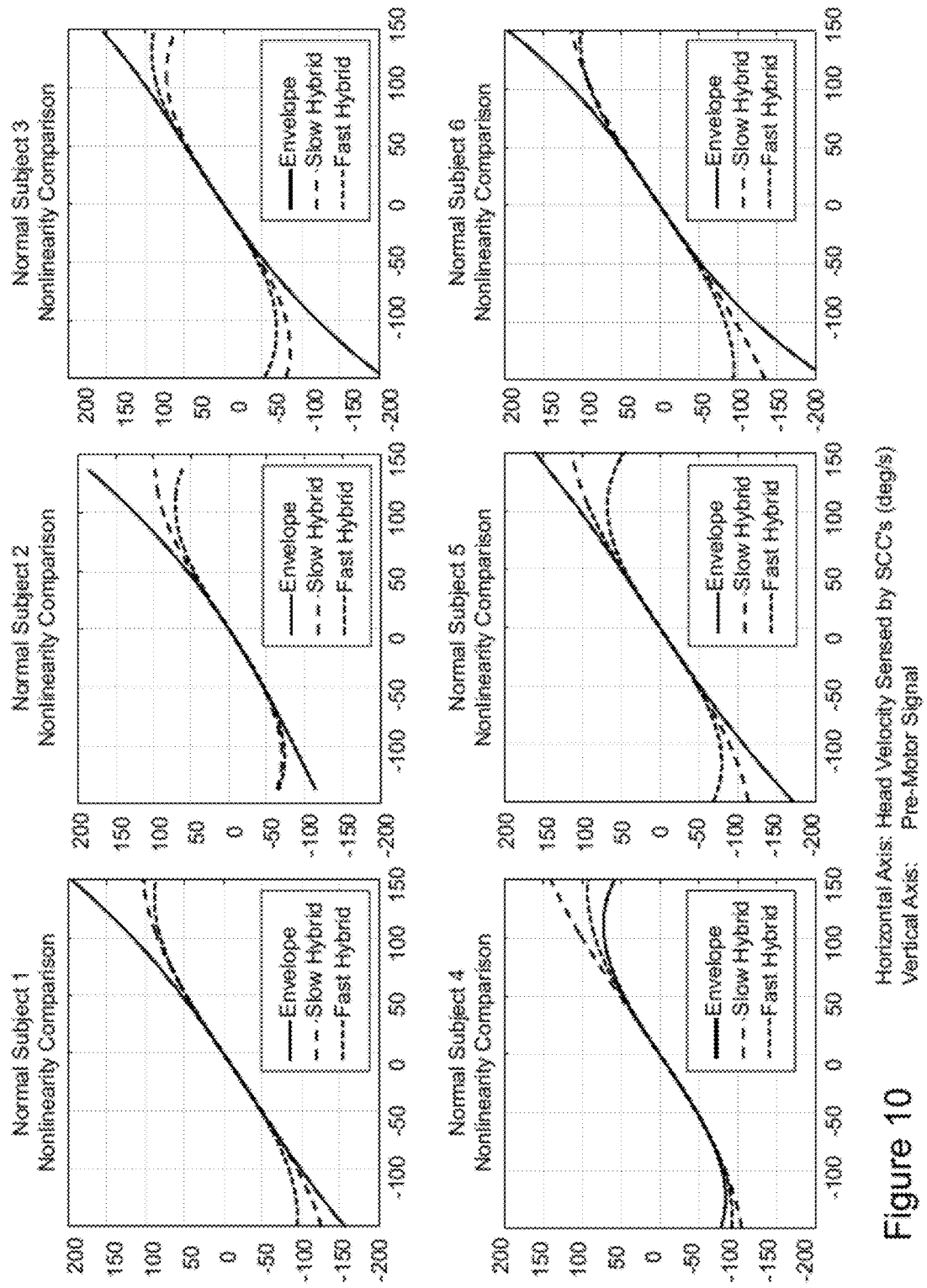
FIG. 10 depicts nonlinear curve estimates associated with the results presented in FIG. 8 derived with an embodiment of the invention, and with the prior art envelope method.

As discussed above, FIG. 7 shows an example of GNL-HybELS performance in classification, nonlinearity estimation, and prediction when applied to one of the normal data sets, normal subject 1. Predictions are made by applying the identified models to the head input signal in the corresponding modes, which are separated by the switching instances estimated through the classification step. FIGS. 8 and 9 respectively contain the estimated transfer functions and their 1 STD error bounds for the normal and patient data respectively. The estimated nonlinearities using GNL-HybELS are plotted, along with nonlinearities estimated instead using the envelope method in FIGS. 10 and 11 for both normal and patient data respectively.

Considering these results the most robust is that within the normal data the fast phase has a larger bandwidth than the slow phase, see FIG. 7. That is, the time constant of the fast phase process is always smaller than that of the slow phase, see Table 2. Additionally, the time constant of the slow phase ranges from 0.6 s to 3.2 s in 5 out of the 6 subjects, a far cry from the expected near perfect integrator assumed in the envelope method of the prior art. Only 1 out of 6 normal subjects exhibited a large time constant, subject 4 with 52 s, though this is traditionally assumed a priori in all cases for the envelope analysis method. The fast phase dynamics are relatively robust given only 6 subjects, with time constants ranging from 125-455 ms (mean 242 ms±140 ms).

TABLE 2

| VOR Analysis Results for Normal Subjects with the GNL-HybELS Algorithm | | | | | | |
|---|---|---|---|---|---|---|
| Normal Subject ID | 1 | 2 | 3 | 4 | 5 | 6 |
| Delay (ms) | 10 | 0 | 0 | 10 | 10 | 10 |
| Canal Time Constant (s) | 20 | 20 | 6 | 12 | 12 | 6 |
| RMS Prediction Error (deg) | 1.5 | 1.2 | .89 | 2.1 | 1.3 | .69 |
| Slow Phase TF (E/H) | $\frac{-.78}{s+.31}$ | $\frac{-.67}{s+.38}$ | $\frac{-.46}{s+.75}$ | $\frac{-.62}{s+.019}$ | $\frac{-.87}{s+.60}$ | $\frac{-.49}{s+1.7}$ |
| Fast Phase TF (E/H) | $\frac{3.9}{s+6.0}$ | $\frac{4.6}{s+8.0}$ | $\frac{2.6}{s+5.9}$ | $\frac{1.0}{s+2.2}$ | $\frac{3.3}{s+2.6}$ | $\frac{2.6}{s+6.6}$ |
| Slow Phase NL Quadratic Coefficient | −7.7e−4 | 4.2e−4 | −4.8e−4 | 7.2e−4 | 1.2e−4 | −3.5e−4 |
| Fast Phase NL Quadratic Coefficient | −1.4e−5 | −2.7e−4 | 7.3e−4 | −3.5e−6 | −5.8e−4 | 9.8e−4 |

The results in patients are more variable, see FIG. 9, but as indicated in Table 3, there is a clear trend towards slower fast phases. As in the normal data, the fast phase transfer function has a larger bandwidth than that of the associated slow phase for each patient, but the distinction is attenuated. This is because the patients exhibit larger time constants for fast phases than those found in normal individual: patients' mean fast phase time constant is 460±172 ms versus mean of 242±140 ms in normal subjects (significant difference at p=0.02).

1200D (denoted GNL-HybELS), while the envelope estimates of the non-linearities always have much larger bounds.

As discussed above the prior art VOR modeling studies have been restricted by the need to pre-classify the nystagmus records, before applying the intended metric estimation. Accordingly, protocols had to be restricted to simple head

TABLE 3

VOR Analysis Results for Patients with the GNL-HybELS Algorithm

| Patient ID | 1 | 2 | 3 | 4 | 5 | 6 |
|---|---|---|---|---|---|---|
| Delay (ms) | 0 | 0 | 10 | 20 | 0 | 10 |
| Canal Time Constant (s) | 20 | 8 | 6 | 20 | 6 | 6 |
| RMS Prediction Error (deg) | 2.1 | 1.6 | 2.1 | 1.3 | .92 | 2.1 |
| Slow Phase TF (E/H) | $\frac{-.52}{s+.69}$ | $\frac{-.48}{s+.52}$ | $\frac{-.67}{s+.79}$ | $\frac{-.60}{s+.96}$ | $\frac{-.50}{s+.59}$ | $\frac{-.83}{s+.51}$ |
| Fast Phase TF (E/H) | $\frac{2.3}{s+2.8}$ | $\frac{.99}{s+1.7}$ | $\frac{1.8}{s+1.6}$ | $\frac{1.9}{s+5.4}$ | $\frac{1.1}{s+1.7}$ | $\frac{2.6}{s+2.4}$ |
| Slow Phase NL Quadratic Coefficient | $-1.3e-3$ | $-5.0e-4$ | $-4.7e-4$ | $-1.2e-3$ | $-2.6e-3$ | $2.3e-3$ |
| Fast Phase NL Quadratic Coefficient | $-2.4e-5$ | $3.1e-4$ | $2.3e-4$ | $-4.0e-6$ | $-9.1e-4$ | $8.6e-4$ |

Considering estimated central non-linearities, the hybrid method supports some degree of non-linearity in the VOR of normal subjects though with consistent symmetry, as evident from the low quadratic coefficients in Table 2. The envelope method on the other hand typically estimates more linear relationships in normal subjects, as shown in FIG. 9. There is agreement at lower head velocities for both methods, with overlap of slope in the lower ranges of head velocity, between ±50 deg/s. In the patient pool, patients 1-5 had right lesions and patient 6 had a left lesion. The results with the hybrid method are consistent with the side of these lesions; the slow phase quadratic coefficients listed in Table 3 are negative for patients 1-5 and positive for patient 6. More intuitively in FIG. 11, the estimated nonlinear curves show an earlier saturation effect on the side of the lesion where positive head velocity values correspond to right-ward motion and negative values to left-ward motion.

Figure 11:
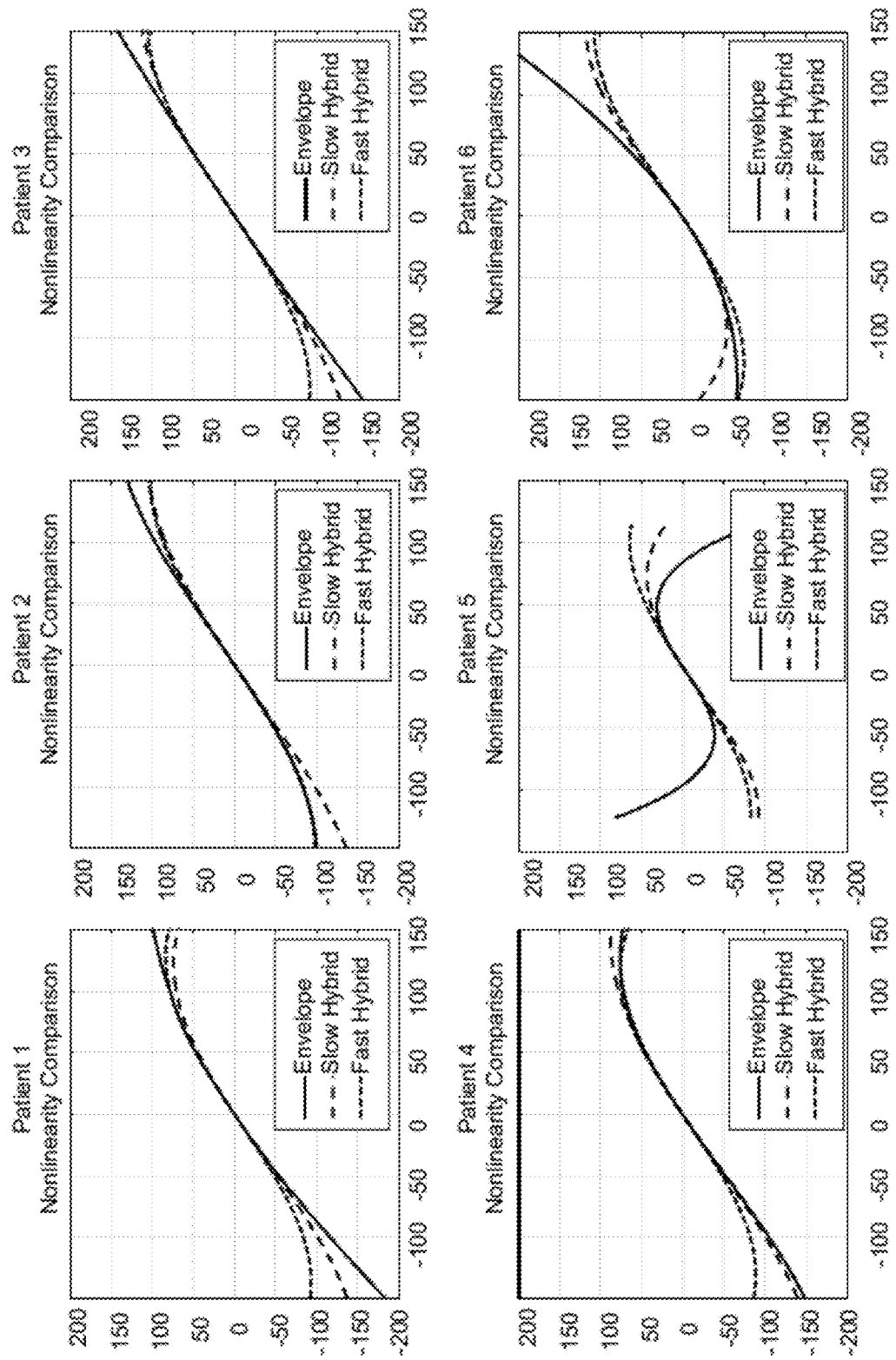
FIG. 11 shows nonlinear curve estimates associated with the results presented in FIG. 8 derived with an embodiment of the invention, and with the prior art envelope method.
Figure 12:
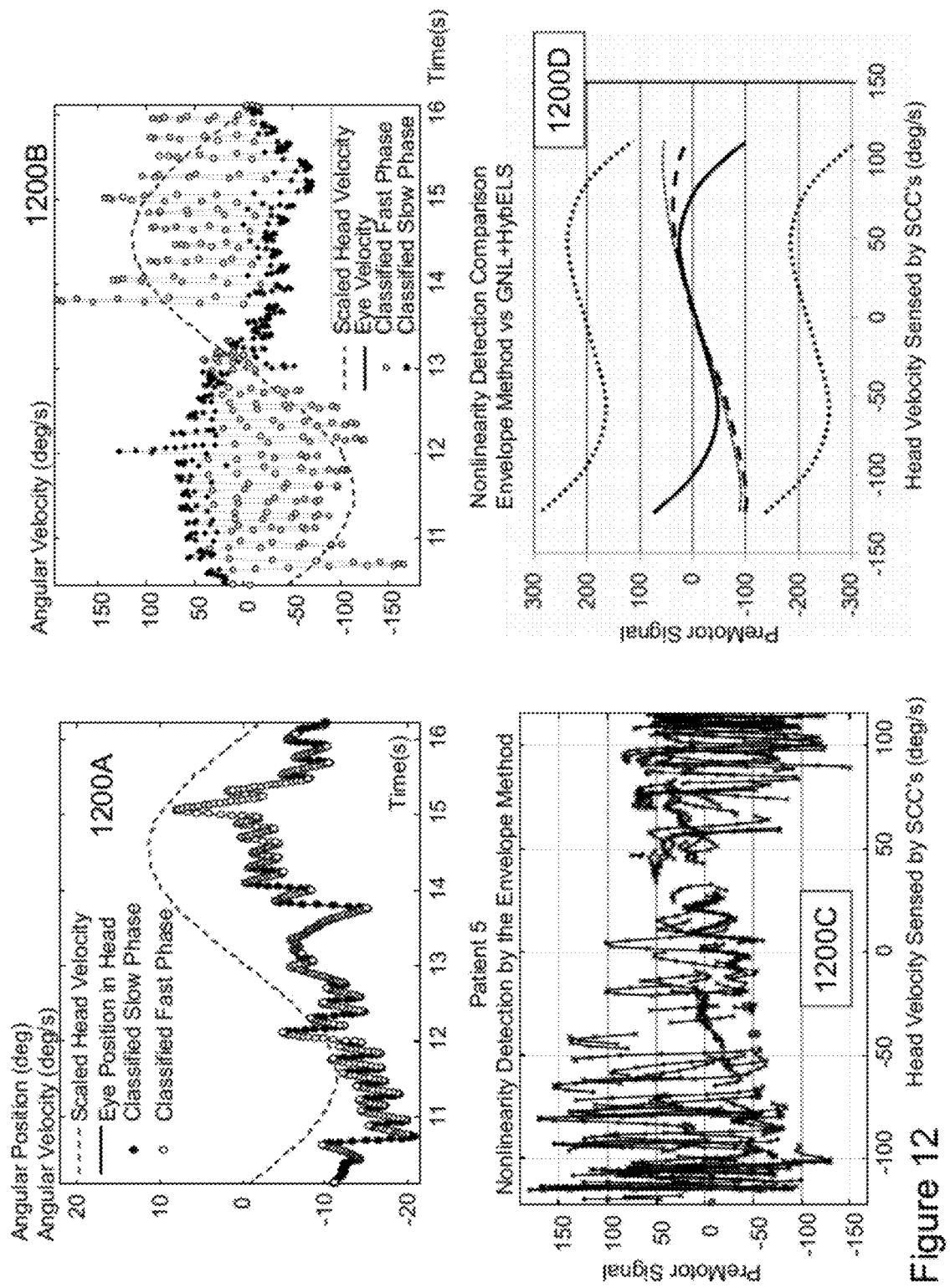
FIG. 12 depicts data and results for patient 5, where envelope method is especially noisy.

It is evident from FIG. 11 that more investigation of Patient 5 is required. The nonlinearity estimated by the envelope method is non-injective for the larger part of its domain. This is not the kind of sensory non-linearity we would expect, because it does not make physiological sense given the sigmoid-like neural behavior. To investigate further, the eye-head velocity trajectories were examined during slow phases that led to this nonlinearity estimate. As shown in FIG. 12 the eye velocity trajectories depicted in first and second graphs 1200A and 1200B during slow phases are very irregular, compared to the simple head velocity harmonic. As a result, the x-y plot 1200C of eye velocity versus head velocity, using these slow phase segments, is very irregular due to the patient's nystagmus pattern. Accordingly the envelope method thus provides a very unreliable and unphysiological estimate of the non-linearity as depicted envelope graph 1200D wherein large STD bounds are evident. Yet the same data segments are well fitted with a robust non-linearity using the hybrid method according to an embodiment of the invention as it is less sensitive to classification errors and switching transients, as demonstrated in the simulation tests above. In fact, the hybrid method according to the embodiment of the invention produced reliable estimates in all cases presented, with small STD bounds similar to those in envelope graph trajectories in order to facilitate the classification step based on the subjective a-priori criteria. More complex protocols were avoided within the prior art as difficult manual scanning/correction of classification was then required. However, complex protocols are actually required and desirable when the goal is to identify reflex dynamics and detect nonlinearities.

In addition, even given pre-classification, the prior art VOR analysis is generally based on fitting "envelopes" through the ensemble of ocular slow-phase segments. Fast phases are not considered part of the clinical VOR. The envelope approach continues to be used to evaluate the compensatory function of the VOR in almost all clinics and laboratories. Yet it is well known that envelopes provide unreliable estimates of the VOR's function and are only applicable under specific conditions:

the so-called neural integrator (NI) in the oculomotor pathways must be very effective with a time constant larger than ~5 s before variable initial conditions on each slow phase segment can be reasonably ignored in the eye velocity traces; and the rotational profiles used in testing the VOR must only contain harmonics above the expected break frequency of the VOR.

This means that envelope analysis of the VOR should not be employed with steps of head rotation, for example, even if the NI satisfies the condition above. Also, if the NI does not satisfy the condition then the envelope analyses will always produce noisy and biased estimates of VOR function which whilst they may be qualitatively useful in coarse evaluations these estimates will miss potential reflex non-linearities, and overestimate the effective time constant of the vestibular sensory process. Nevertheless, envelopes are still commonly used in medical clinics for the diagnosis of abnormalities, even though the results above give clear examples that most subjects do not satisfy the assumptions. The clinical consequences are that some vestibular patients may be judged to have compensated for a unilateral vestibular lesion when in fact the deficit remains. This can be seen in the plots of FIG. 10 where the envelope estimates of VOR symmetry are often more linear than a more appropriate hybrid analysis. Interestingly, when the assumptions of the envelope method are valid, then the envelope and hybrid methods give similar estimates for the slow phase nonlinearity, see for example normal subject 4 with larger slow phase time constant in FIG. 10. On the other hand, the envelope methods give more disparate results when the slow phase time constants are much smaller, for example normal subjects 3 and 6 in FIG. 10.

According to the invention presented here by the inventors, classification and VOR reflex identification are performed simultaneously, objectively, and automatically thereby providing a significant enhancement over the prior art and general deployment of the technique without expert involvement. The results of the GNL-HybELS approach presented by the inventors according to an embodiment of the invention have been demonstrated to be accurate and robust to both measurement noise and to moderate classification errors. Importantly, the algorithms according to embodiments of the invention can identify simultaneously all modes embedded in a system response. Accordingly, embodiments of the invention can provide estimates of input delays, static sensory non-linearities, and the linear dynamics of modes in a hybrid system, while classifying the data at the same time.

Algorithms according to embodiments of the invention can also estimate the effective vestibular time constant in VOR applications or other sensory preprocessing stages in more general ocular reflexes. One need only propose reasonable orders for dynamic stages, and decide which stage can be time continuous, and which can be hybrid or switching. For example in the VOR, the vestibular sensory signals can be considered continuous, while the premotor areas in the brainstem are known to switch or change their characteristics during slow and fast phases of nystagmus. In addition, this approach also makes it possible to use any testing protocol or protocols without considering the difficulties of classification, and instead focusing on the best tests to unmask the particular dynamics for analysis or diagnosis.

Figure 13:
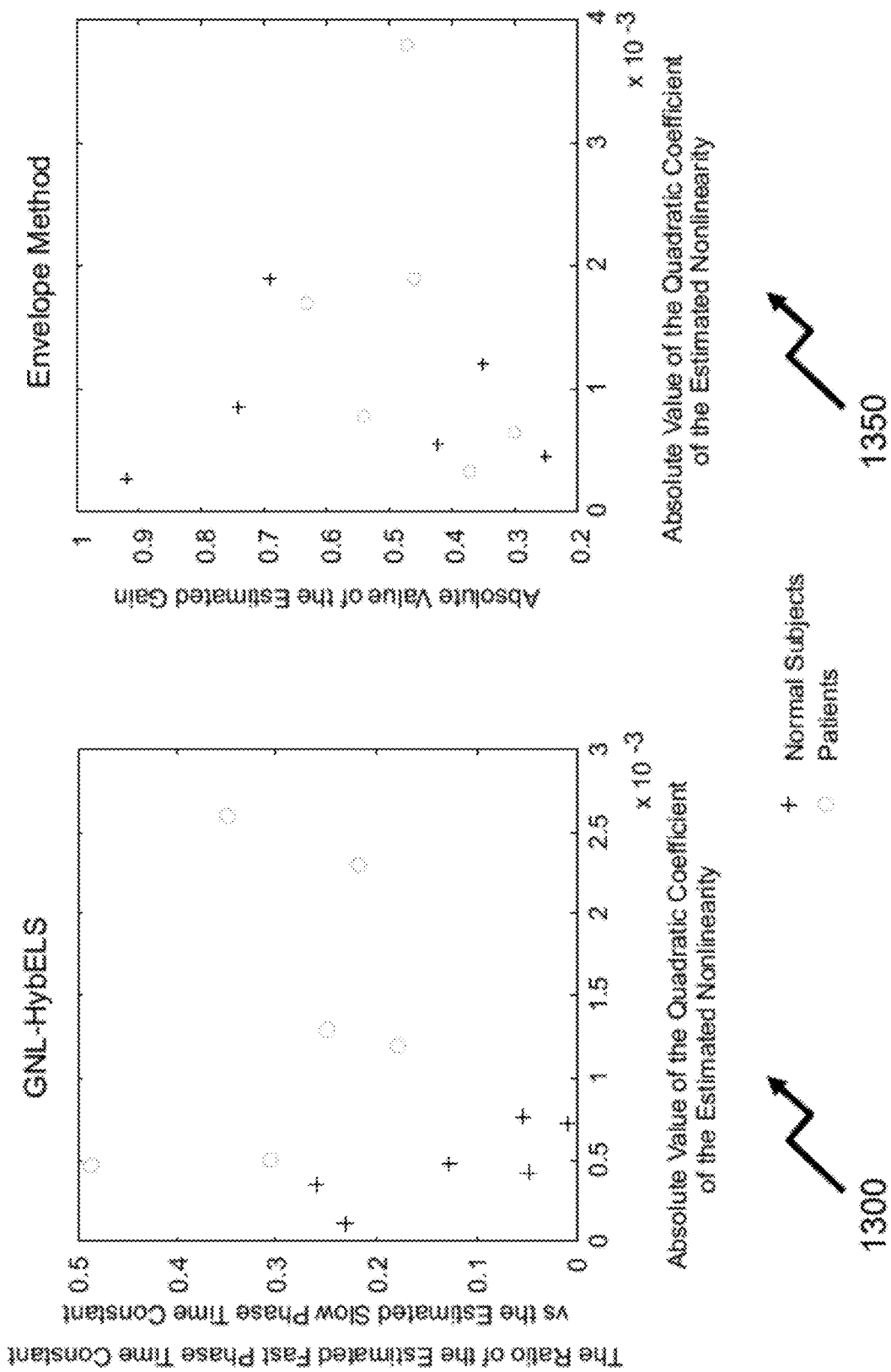
FIG. 13 shows a comparison of the quadratic coefficients estimates using the invention and the current state of the art for data relating to normal subjects and patients.

The experimental results are promising from the clinical point of view. Since the components being estimated are better aligned to the known physiology, results are more robust and appear to have more diagnostic power than the parameters available from the prior art envelope analysis methods. For example, normal subjects were shown in FIG. 10 to generally have a smaller quadratic term in their identified non-linearity, which means their VOR system is more "symmetric". They also have a more pronounced difference between their slow and fast phase time constants, which means the VOR dynamics in the two modes are more distinct. Plotting the ratio of identified slow and fast time constants versus the level of the quadratic term in the non-linear curve segregates well the 6 normal subjects from the 6 patients as shown in FIG. 13 with GNL-HybELS graph 1300. In contrast, the envelope method results only provide a noisy non-linear estimate, a vestibular time constant and gain, all for the slow-phase with nothing for the fast phase. Similarly in FIG. 13, the envelope graph 1350 plotting the ratio of identified slow and fast time constants versus the level of the quadratic term in the non-linear curve cannot separate patients from normal subjects thereby demonstrating the weaknesses of the prior art as a diagnostic method.

Additionally, embodiments of the invention can also be used in a wider range of clinical applications. Apart from the above-mentioned bimodal approach, the nystagmus records can be probed in order to pose questions related to the sites of deficits and/or the pathways affected. For example by addressing differences between slow phases versus fast phases and/or directional deficits. Inferences can then be made on potential connections in VOR pathways that have not yet been documented experimentally by neurophysiologists.

Further, the GNL-HybELS approach according to embodiments of the invention can be used to classify the data into any number of classes until identification and prediction errors are optimized. For instance, the dynamics of the rightward and leftward fast eye movements could in principle be different since they rely on a different subset of bursting cells ipsilateral to the fast phase direction. Similarly, the dynamics of slow phases in different directions could be different, since the premotor cells in the brainstem are interconnected with other nuclei such as the Prepositus Hypoglossi and cerebellar sites, all driven by ipsilateral canal signals.

Figure 14A:
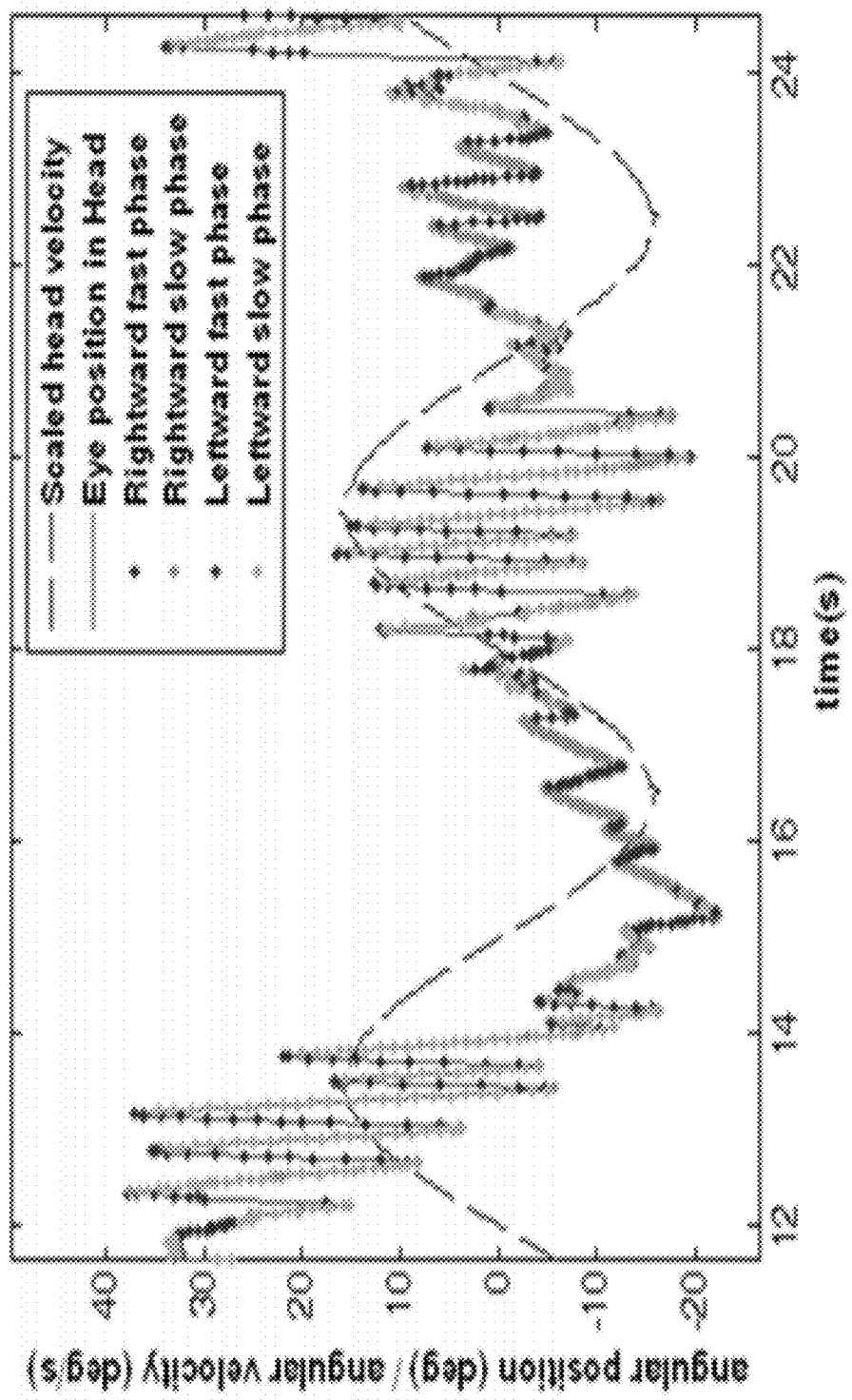
FIG. 14A depicts classification results derived from data for Patient 6 using an algorithm according to an embodiment of the invention, with auto-segmentation of rightward and leftward slow and fast phases.
Figure 14B:
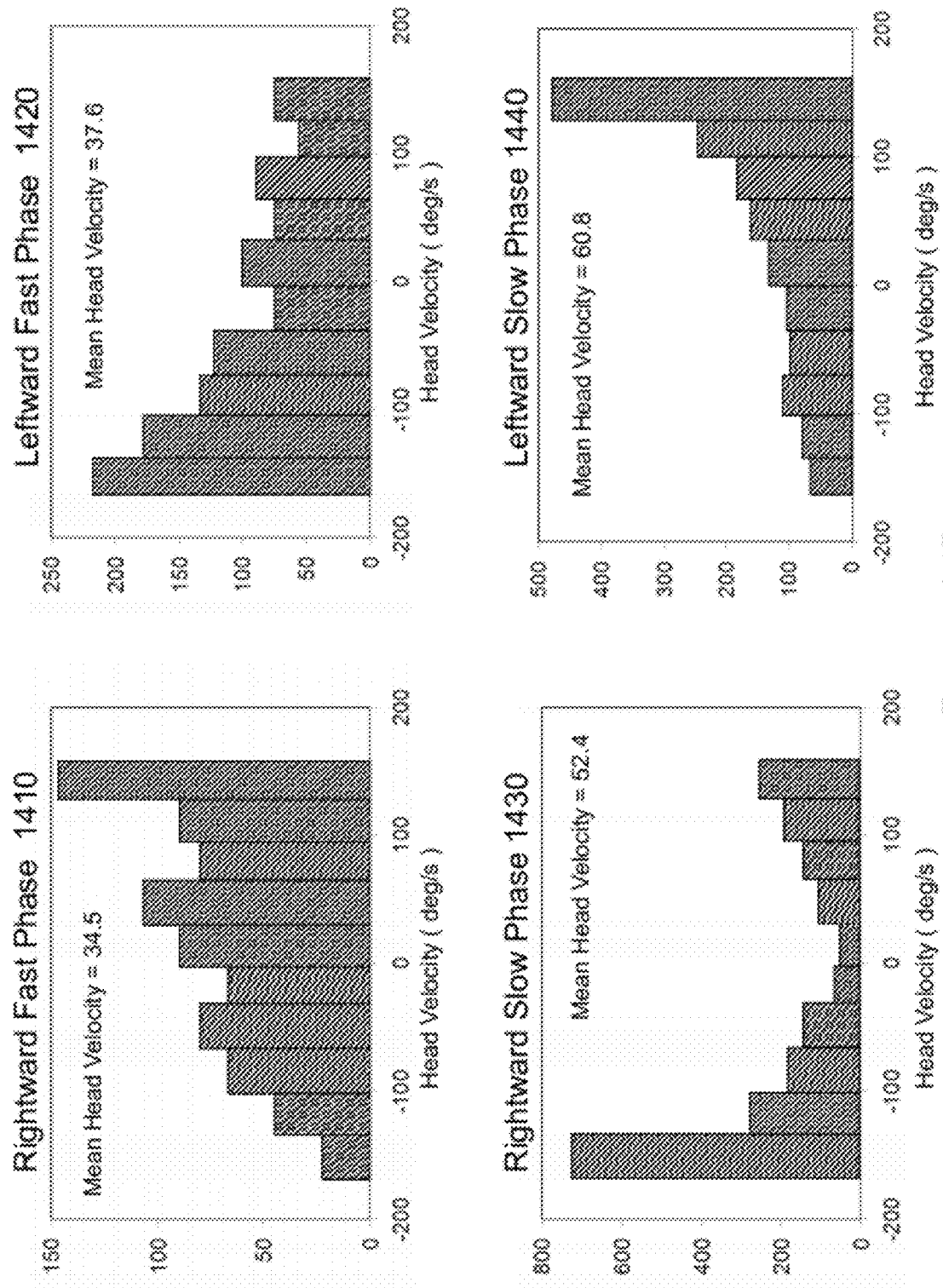
FIG. 14B depicts the histograms of these results with head velocity.

Accordingly, for example in patients with unilateral lesions or deficits, one might expect that dividing the nystagmus records into more classes would provide better modeling accuracy. FIGS. 14A and 14B demonstrate one such case for Patient 6 wherein the GNL-HybELS method according to an embodiment of the invention was set to automatically classify the data into 4 classes, these in this instance turning out to be rightward and leftward slow phases, and rightward and leftward fast phases. The resulting classification groups are plotted in FIG. 14A which when analysed are associated with a broad range of head velocities as shown from the first to fourth histograms 1410 through 1440 in FIG. 14B which are fast rightward, fast leftward, slow rightward and slow leftward respectively. As is evident in second histogram 1420, classified leftward fast phases are not all associated with leftward head velocity. This again demonstrates that a manual classification likely would have failed, given the usual assumption that fast phases are always in the direction of head velocity, yet the automated classification was consistent when examined in the context of 'gaze' (eye+head=gaze in space) redirection. Referring to Table 4 there are listed the identified linear dynamics in the form of transfer functions for all the classes.

It is evident from these results that this patient. Patient 6, has abnormalities in the rightward slow phase, and the leftward fast phase, both of which correspond to activation of premotor cells on the left brainstem, typically during left head movements. The gains in these cases are very low compared to normal subjects, and the leftward fast phase time constant is much higher than that of normal subjects, i.e. the leftward fast phase is quite slow. This is consistent with the fact that this patient has a left lesion and would imply a unilateral vestibular role in driving rapid eye movements. In other words, this type of result asks the question whether vestibular signals are involved during fast phases, and whether they might be arising from a single canal. This has not yet been tested by neurophysiologists, and in fact it is often assumed that the VOR is turned off during saccades. Such inferences are actually only possible when dealing with patients with known unilateral deficits, and with the help of hybrid identification tools. In normal subjects, the bilateral vestibular systems are typically similar enough to make it difficult to ask such questions.

TABLE 4

Transfer Functions for Classes using GNL-HybELS

|  | Slow Phase | Fast Phase |
| --- | --- | --- |
| Rightward movement | $\frac{-.32s}{s+.18}$ | $\frac{2.3s}{s+5.4}$ |
| Leftward movement | $\frac{-.99s}{s+.10}$ | $\frac{.63s}{s+.75}$ |

Figure 15:
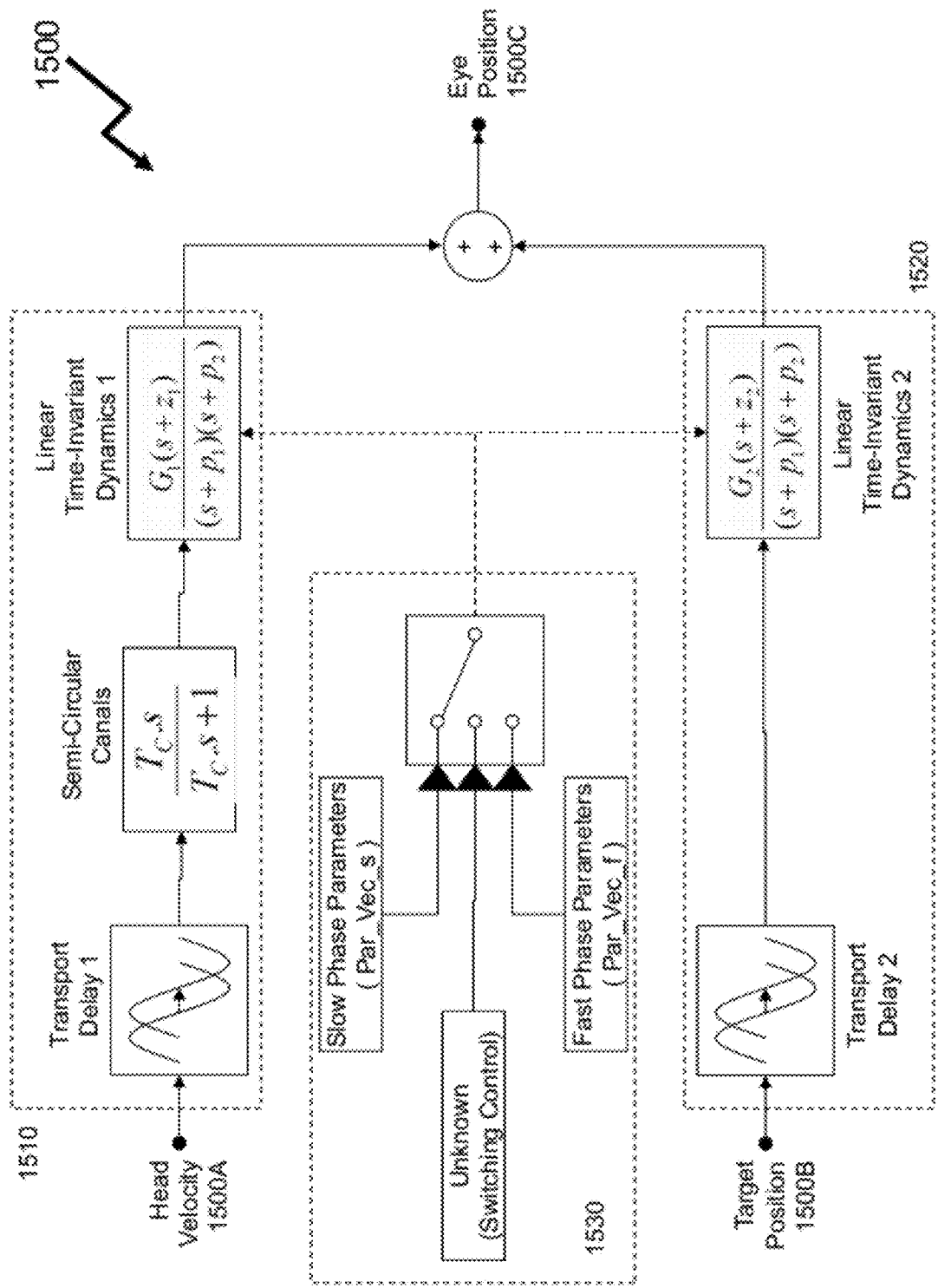
FIG. 15 depicts a multi-input system for vision and vestibular stimuli which can be analyzed according to embodiments of the invention.

The GNL-HybELS approach according to embodiments of the invention can also be used to identify other neural systems with similar behavior, such as postural or reaching movements that exhibit discrete dynamics within given time intervals. For example the inventors have applied it to multiple-input systems such as the one depicted in FIG. 15, where various oculomotor subsystems such as the VOR, smooth pursuit, or the saccadic systems are active simultaneously (visual-vestibular interactions). Accordingly inputs are head velocity 1500A and target position 1500B which are processed using first and second analysis paths 1510 and 1520 respectively wherein in each path the linear time-invariant dynamic characteristics are coupled to the switching block 1530 so that both are in the same 'mode' at any given time. Accordingly, analysis using the techniques described above in respect of embodiment of the invention would enable those skilled in the art to study and compare the dynamics of these systems when operating in isolation and in cooperation and accordingly establish similar tests and analysis to identify patients suffering particular deficits from normal subjects and potentially further classify patients to specific deficits.

The techniques according to embodiments of the invention can be considered a new general tool allowing increased freedom in the design of experimental protocols for research and clinical investigations into sensory-motor integration. These protocols no longer need be kept simple, in order to facilitate manual classification of nystagmus records. Instead classification and identification can be done in complex tasks, based simply on the detection of dynamic consistency across subintervals in a data record.

It would also be evident to one skilled in the art that the characterization of discreet and combined oculomotor subsystems including but not limited to VOR, smooth pursuit, or the saccadic systems allows statistically significant populations of data to be derived rapidly and independent of expert intervention such that these techniques may be considered in the future as part of routine patient testing protocols in clinics, hospitals etc. and even in the field away from medical facilities. Additionally, these techniques may be applied to other aspects of human systems including for example postural or reaching movements that exhibit discrete dynamics within given time intervals and embodiments of the invention can provide estimates of input delays, static non-linearities, and the linear dynamics of the modes in these hybrid systems, while classifying the data at the same time.

Within the descriptions above in respect of embodiments of the invention, emphasis has been placed on the application of the approaches taught to human based hybrid systems. However, it would be evident to one skilled in the art that the principles may be applied equally to non-human species as well as robotic systems. For example, robotic locomotion has been studied using a wide range of wheeled and legged robots. Although wheeled robots move quickly, they can only move on smooth terrain or terrain with low topography and lack the versatility of legged robots in handling rough terrain. As a result, there has been a concerted effort within the robot community to understand the motion of legged robots. The motion of the biped and quadruped robots causes the head and the cameras mounted on them to pitch, yaw, and roll and linearly accelerate in three dimensions. The very fact that legged motion generates this kind of disturbance makes it difficult to keep the visual frame stable. Humanoid Robots and Quadruped robots are therefore in need of a strong sense of awareness in terms of its position and its movements in space. One approach to solving this problem is to develop an artificial vestibular system and implement gaze stabilization techniques on robots that have a binocular camera system mounted on their heads and are capable of individual or common rotations.

Accordingly, the algorithms according to embodiments of the invention may be applied equally in these other non-human and robotic systems to determine eye motion in response to motion of their mounting platform, commonly the head. Additionally, such control algorithms may also be applied in other robotic systems such as those that are air, aquatic and space based in order to stabilize the vision systems of these robotic systems in order to provide improved fixed object viewing, smooth pursuit, etc. Accordingly, embodiments of the invention and outcomes from embodiments of the invention may be deployed as software routines within autonomous and non-autonomous robotic systems.

Figure 16:
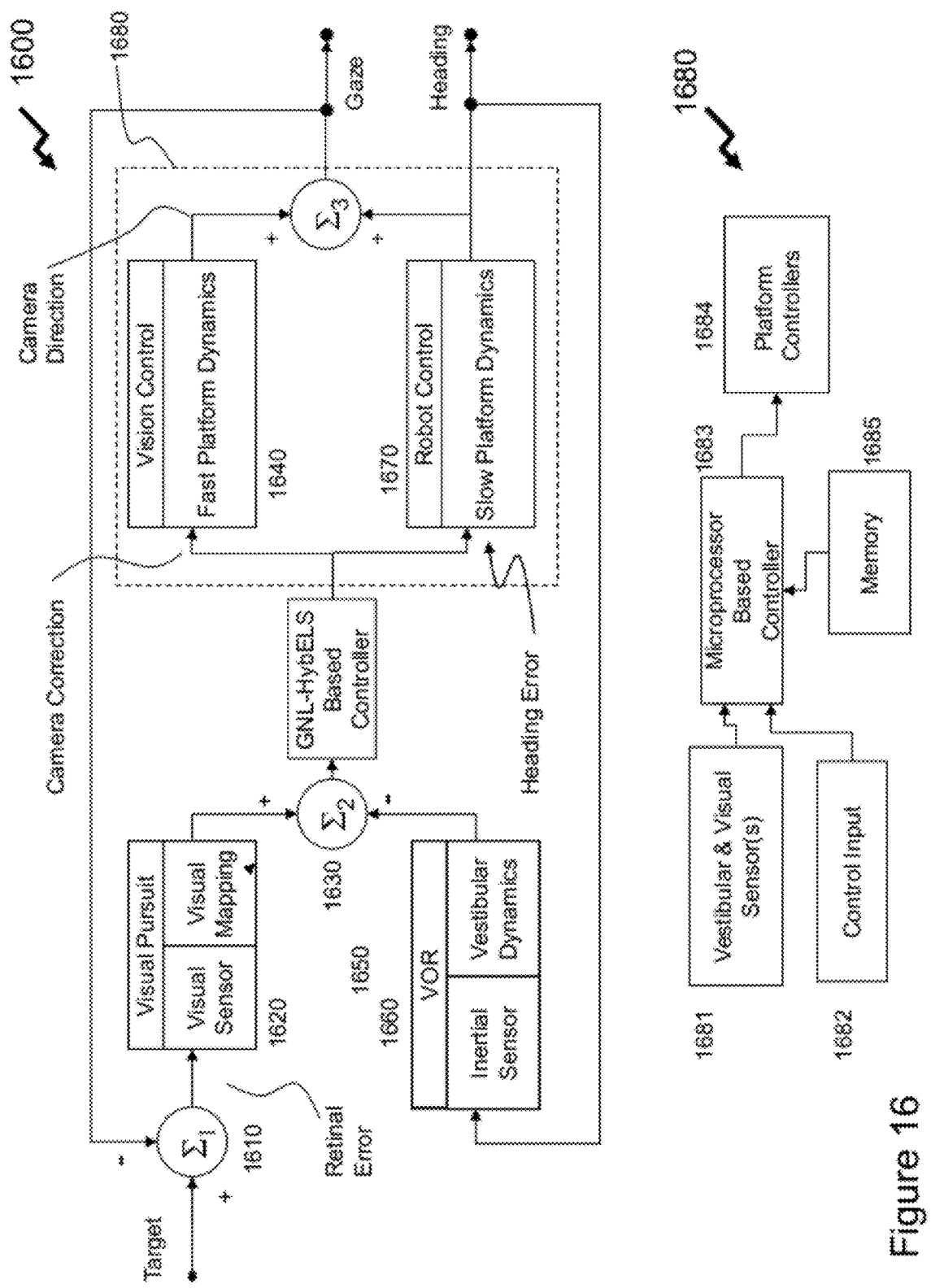
FIG. 16 depicts a control system for a robotic system exploiting a vestibulo-ocular reflex process interacting with visual goals as an embodiment of the invention.

For example in FIG. 16 a robotic vision control system 1600 is presented that summarizes interactions between sensory feedback networks involved in the control of a robotic platform. The control system depicted in robotic vision control system 1600 has one input, Target, and generates two outputs, Gaze and Heading. In this example the "steering by gazing" control strategy aims at making Gaze and Heading, i.e. the complete robot, follow any variation in the Target. For example such a robotic vision control system 1600 may be employed in vision-based steering control system for aerial vehicles. The mechanical decoupling between the eye and the body is here modeled by the robot block where the unique control input signal is split into one input reference for controlling the eye's (camera) orientation and another signal for controlling the robot's heading. For a stationary target, the control system will compensate for any disturbances applied to the body by holding the gaze locked onto the target. For a moving target, the control system will change both the eye's orientation and the robot's heading to track smoothly the target.

Let us look at the path involving the "vestibulo-ocular reflex" (VOR) block 1660 and the vision control 1640 blocks in robotic vision control system 1600. The minus sign on second summation 1630 means that any rotation of the head will be compensated for by a counter rotation of the eye and head (but more slowly). Robotic vision control system 1600 also shows two feedback loops controlling both a fast low-inertia plant, the vision control 1640, and a slow high-inertia plant, the robot control 1670. The first of these controls the eye's orientation by the visual feedback-loop from the output "Gaze" back to the first summation 1610 with the "Target" and feedback of any head perturbations based on the VOR block 1660. The second of these relating to the robot's heading is controlled by an inertial feedback-loop wherein an estimate of the heading deduced from the robot's rotational speed measured by a rate gyro or equivalent sensor is provided as the input to the VOR block 1660. As shown these two control feedback-loops are merged by using the second summation 1630 where the estimated robot's heading becomes an input disturbance for the visual feedback-loop, whereas the retinal error becomes a reference input for the inertial feedback-loop.

Accordingly control system 1680 may be implemented within robotic systems. Rotational and longitudinal sensor inputs are mixed with visual signals (block 1681) received by a microprocessor based controller 1683. The controller state (mode) would be selected according to control input data from block 1682, defined by GNL-HybELS. This data is employed in conjunction with the VOR algorithm stored within memory 1685 to provide control settings to the rotational and translation controllers 1684 of the robotic platform and 1640 of the Vision platform. In the absence of specific goals for the robot heading, distinct from the visual goal, the robot would generally aim itself along the direction of the visual target. An alternative embodiment could add a separate spatial goal (heading) for the robotic platform by computing and inserting an additional input of Heading Error control signal to block 1670.

It would be clear to one skilled in the art that this approach to multi-task and multi-sensor fusion could be raised to higher complexities including, but not limited to:

- a shared sensory-derived fusion of all sensory errors sent to all participating platforms, related to execution of a visual orientation task (e.g. cameras and supporting elements in a robot)
- execution of error reduction to occur with dynamics in either a fast mode (re-orient) or a slow mode (stable posture) in all platforms, the latter set in the same mode at any given time, as controlled by GNLHybELS switching controller
- without an explicit heading goal (Heading error=0), the robot heading would default to aligning itself roughly with the target.
- with an explicit heading goal different from the visual goal, an associated heading error would pass only to the supporting robot (Heading error, extended application), in addition to the previous sensory-derived error merging visual error with vestibular perturbations.

This example allows two goals to be met simultaneously: a visual one reflected first on the lightest element (camera) with the help of slower support platforms, and a postural one focused on heavier support platforms (e.g. global heading). Several other embodiments with increasing goals would be evident to one skilled in the art.

It would be evident to one skilled in the art that the resulting models and analysis of the vestibulo-ocular reflex may be exploited in environments other than patient diagnosis, patient monitoring, and robotic systems. For example it is known that the human vestibulo-ocular reflex can adjust or adapt to relatively low magnifications of the viewed image as may exist for example through varying prescription eye glasses or contact lenses and the use of magnifying systems such as magnifying glasses, binoculars, and microscopes. Additionally, combinations of these elements may be present within different environments such as head-up displays, night-vision systems, head or helmet mounted displays, and artificial environments such as artificial reality and simulators. Accordingly, models of the vestibulo-ocular reflex for different populations of individuals may be applied to predicting aspects of that population of individuals to particular environments and/or visual stimuli in order to adjust characteristics of optical systems to that population.

For example, patients suffering visual impairments resulting from disease, trauma, or congenital or degenerative conditions that cannot be corrected by current conventional means, such as refractive correction, medication, or surgery may benefit from adjustment in the correction provided that factors their particular VOR characteristics into the equation. Similarly, patients with eye disorders leading to visual impairments, which may include but not be limited to retinal degeneration, albinism, cataracts, glaucoma, muscular problems that result in visual disturbances, corneal disorders, diabetic retinopathy, congenital disorders, and infection, may likewise benefit from consideration of their specific VOR characteristics in designing or implementing corrective methods. Similarly visual impairment caused by brain and nerve disorders, usually termed cortical visual impairments (CVI), may be similarly factored in.

For example, wearable, electronic assistive technologies may incorporate one or more high-resolution video cameras in conjunction with near-to-eye video screens. Such devices in order to remove user symptoms as evident from experiences of trainees and gamers with simulators and virtual reality environments may be modeled and simulated to account for the user's VOR. Clearly a user wearing such an assistive technology is immersed for substantial periods unlike simulators and virtual reality gamers such that subtle effects not evident in such environments can become significant in assistive situations and hence the actual VOR of different patient classes and/or patients a factor in the design and implementation of such assistive technologies wherein establishing a VOR model for that patient class and/or patient is a step in the appropriate technology solution.

As discussed above it would also be evident to one skilled in the art that the invention may be applied to a variety of other systems wherein the characteristic of the system may be simulated and/or modeled using a combination of static nonlinearity parameters and linear dynamic parameters. Such characteristics and systems may for example include motion of a user's limb or a user's finger. For example, touching a fixed point with the human finger whilst the user is moving or the reverse requires similar linear and non-linear dynamics to achieve the required result.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may vary in implementation where the memory is employed in storing software codes for subsequent execution to that when the memory is employed in executing the software codes. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels and/or various other mediums capable of storing, containing or carrying instruction(s) and/or data.

The methodologies described herein are, in one or more embodiments, performable by a machine which includes one or more processors that accept code segments containing instructions. For any of the methods described herein, when the instructions are executed by the machine, the machine performs the method. Any machine capable of executing a set of instructions (sequential or otherwise) that specify actions to be taken by that machine are included. Thus, a typical machine may be exemplified by a typical processing system that includes one or more processors. Each processor may include one or more of a CPU, a graphics-processing unit, and a programmable DSP unit. The processing system further may include a memory subsystem including main RAM and/or a static RAM, and/or ROM. A bus subsystem may be included for communicating between the components. If the processing system requires a display, such a display may be included, e.g., a liquid crystal display (LCD). If manual data entry is required, the processing system also includes an input device such as one or more of an alphanumeric input unit such as a keyboard, a pointing control device such as a mouse, and so forth.

The memory includes machine-readable code segments (e.g. software or software code) including instructions for performing, when executed by the processing system, one of more of the methods described herein. The software may reside entirely in the memory, or may also reside, completely or at least partially, within the RAM and/or within the processor during execution thereof by the computer system. Thus, the memory and the processor also constitute a system comprising machine-readable code.

In alternative embodiments, the machine operates as a standalone device or may be connected, e.g., networked to other machines, in a networked deployment, the machine may operate in the capacity of a server or a client machine in server-client network environment, or as a peer machine in a peer-to-peer or distributed network environment. The machine may be, for example, a computer, a server, a cluster of servers, a cluster of computers, a web appliance, a distributed computing environment, a cloud computing environment, or any machine capable of executing a set of instructions (sequential or otherwise) that specify actions to be taken by that machine. The term "machine" may also be taken to include any collection of machines that individually or jointly execute a set (or multiple sets) of instructions to perform any one or more of the methodologies discussed herein.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method comprising:
   (i) receiving input-output data relating to a characteristic of a system;
   (ii) establishing with a microprocessor an estimate of at least one hybrid state of a plurality of hybrid states of the system;
   (iii) establishing with the microprocessor in dependence upon at least the estimate a classification of the input-output data and an identification of a dynamic aspect of the system;
   (iv) selecting at least one of classification of the input-output data and the identification of the dynamic aspect of the system in dependence upon errors of each with respect to the input-output data;
   (v) generating a new estimate of the at least one hybrid state of a plurality of hybrid states of the system in dependence upon the selected at least one of classification of the input-output data and the identification of the dynamic aspect of the system;
   (vi) iterating steps (iii), (iv) and (v) until a predetermined condition is satisfied;
   (vii) detecting with the microprocessor at least one non-linearity of a plurality of non-linearities in dependence upon at least the input-out data and the selected at least one of classification of the input-output data and the identification of the dynamic aspect of the system;

(viii) adjusting a parameter relating to the dynamic aspect of the system determined from the iterative analysis in dependence upon at least the non-linearity of the plurality of non-linearities; and (ix) determining at least one of a static non-linearity parameter of a plurality of static non-linearity linear dynamic parameters and a linear dynamic parameter of a plurality of linear dynamic parameters, wherein;

performing an initial analysis comprises at least one of;

segmenting at least one subspace of a plurality of subspaces and the corresponding normal for the at least one subspace from the input-output data, each subspace characterized by at least one of a fixed dimension and a variable dimension; and establishing an initial setting for at least one time constant of a plurality of time constants relating to the system, establishing an initial setting for at least one delay constant of a plurality of delay constants relating to the system, and performing at least one of an initial classification of the input-output data and an initial identification of a dynamic aspect of the system.

2. The method according to claim 1 wherein;
the at least one delay constant of the plurality of delay constants relates to the delay between the input and the output; and
the at least one time constant of the plurality of time constants relates to a characteristic of at least one of the human eye and the human ear.

3. The method according to claim 1 wherein;
the steps of performing the initial analysis and iterating are performed absent an a priori assumption.

4. The method according to claim 1 wherein;
establishing with the microprocessor in dependence upon at least the estimate a classification of the input-output data and an identification of a dynamic aspect of the system comprises generating at least a first model using the current classification parameters of the system and a second model using the current dynamic parameters of the system.

5. A system comprising:
a microprocessor;
a first non-transitory tangible computer readable medium for storing input-output data relating to a characteristic of a monitored system;
a non-transitory tangible computer readable medium encoding a computer program for execution by the microprocessor, the computer program comprising the steps of (i) receiving input-output data relating to a characteristic of a system;

(ii) establishing with a microprocessor an estimate of at least one hybrid state of a plurality of hybrid states of the system;

(iii) establishing with the microprocessor in dependence upon at least the estimate a classification of the input-output data and an identification of a dynamic aspect of the system;

(iv) selecting at least one of classification of the input-output data and the identification of the dynamic aspect of the system in dependence upon errors of each with respect to the input-output data;

(v) generating a new estimate of the at least one hybrid state of a plurality of hybrid states of the system in dependence upon the selected at least one of classification of the input-output data and the identification of the dynamic aspect of the system;

(vi) iterating steps (iii), (iv) and (v) until a predetermined condition is satisfied;

(vii) detecting with the microprocessor at least one non-linearity of a plurality of non-linearities in dependence upon at least the input-out data and the selected at least one of classification of the input-output data and the identification of the dynamic aspect of the system;

(viii) adjusting a parameter relating to the dynamic aspect of the system determined from the iterative analysis in dependence upon at least the non-linearity of the plurality of non-linearities; and (ix) determining at least one of a static non-linearity parameter of a plurality of static non-linearity linear dynamic parameters and a linear dynamic parameter of a plurality of linear dynamic parameters, wherein;

performing an initial analysis comprises at least one of;

segmenting at least one subspace of a plurality of subspaces and the corresponding normal for the at least one subspace from the input-output data, each subspace characterized by at least one of a fixed dimension and a variable dimension; and establishing an initial setting for at least one time constant of a plurality of time constants relating to the system, establishing an initial setting for at least one delay constant of a plurality of delay constants relating to the system, and performing at least one of an initial classification of the input-output data and an initial identification of a dynamic aspect of the system.

6. The system according to claim 5 wherein;
the at least one delay constant of the plurality of delay constants relates to the delay between the input and the output; and
the at least one time constant of the plurality of time constants relates to a characteristic of at least one of the human eye and the human ear.

7. The system according to claim 5 wherein;
the steps of performing the initial analysis and iterating are performed absent an a priori assumption.

8. The system according to claim 5 wherein;
establishing with the microprocessor in dependence upon at least the estimate a classification of the input-output data and an identification of a dynamic aspect of the system comprises generating at least a first model using the current classification parameters of the system and a second model using the current dynamic parameters of the system.

9. A non-transitory tangible computer readable medium encoding a computer program for execution by the microprocessor, the computer program comprising the steps of:

(i) receiving input-output data relating to a characteristic of a system;

(ii) establishing with a microprocessor an estimate of at least one hybrid state of a plurality of hybrid states of the system;

(iii) establishing with the microprocessor in dependence upon at least the estimate a classification of the input-output data and an identification of a dynamic aspect of the system;

(iv) selecting at least one of classification of the input-output data and the identification of the dynamic aspect of the system in dependence upon errors of each with respect to the input-output data;

(v) generating a new estimate of the at least one hybrid state of a plurality of hybrid states of the system in dependence upon the selected at least one of classification of the input-output data and the identification of the dynamic aspect of the system;

(vi) iterating steps (iii), (iv) and (v) until a predetermined condition is satisfied;

(vii) detecting with the microprocessor at least one non-linearity of a plurality of non-linearities in dependence upon at least the input-out data and the selected at least one of classification of the input-output data and the identification of the dynamic aspect of the system;

(viii) adjusting a parameter relating to the dynamic aspect of the system determined from the iterative analysis in dependence upon at least the non-linearity of the plurality of non-linearities; and (ix) determining at least one of a static non-linearity parameter of a plurality of static non-linearity linear dynamic parameters and a linear dynamic parameter of a plurality of linear dynamic parameters, wherein;

performing an initial analysis comprises at least one of;
segmenting at least one subspace of a plurality of subspaces and the corresponding normal for the at least one subspace from the input-output data, each subspace characterized by at least one of a fixed dimension and a variable dimension; and
establishing an initial setting for at least one time constant of a plurality of time constants relating to the system, establishing an initial setting for at least one delay constant of a plurality of delay constants relating to the system, and performing at least one of an initial classification of the input-output data and an initial identification of a dynamic aspect of the system.

10. The non-transitory tangible computer readable medium encoding a computer program for execution by the microprocessor according to claim 9 wherein;
the at least one delay constant of the plurality of delay constants relates to the delay between the input and the output; and
the at least one time constant of the plurality of time constants relates to a characteristic of at least one of the human eye and the human ear.

11. The non-transitory tangible computer readable medium encoding a computer program for execution by the microprocessor according to claim 9 wherein;
the steps of performing the initial analysis and iterating are performed absent an a priori assumption.

12. The non-transitory tangible computer readable medium encoding a computer program for execution by the microprocessor according to claim 9 wherein;
establishing with the microprocessor in dependence upon at least the estimate a classification of the input-output data and an identification of a dynamic aspect of the system comprises generating at least a first model using the current classification parameters of the system and a second model using the current dynamic parameters of the system.

* * * * *